US009332776B1

(12) United States Patent
Beetz et al.

(10) Patent No.: US 9,332,776 B1
(45) Date of Patent: *May 10, 2016

(54) METHODS AND APPARATUS FOR LOW HEAT SPRAY DRYING

(71) Applicant: ZoomEssence, Inc., Sayreville, NJ (US)

(72) Inventors: Charles P. Beetz, Erlanger, KY (US); Robert Corbett, Westfield, NJ (US); David Salem, Rapid City, SD (US)

(73) Assignee: ZOOMESSENCE, INC., Sayreville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/606,771

(22) Filed: Jan. 27, 2015

Related U.S. Application Data

(63) Continuation-in-part of application No. 13/245,369, filed on Sep. 26, 2011, now Pat. No. 8,939,388.

(60) Provisional application No. 61/386,762, filed on Sep. 27, 2010.

(51) Int. Cl.
*A61K 47/00* (2006.01)
*A23L 1/22* (2006.01)
(Continued)

(52) U.S. Cl.
CPC ............ *A23L 1/22016* (2013.01); *A23L 1/0029* (2013.01); *A61K 9/16* (2013.01); *A61K 9/1652* (2013.01); *C11B 9/00* (2013.01); *A23V 2002/00* (2013.01)

(58) Field of Classification Search
CPC ... A61K 38/28; A61K 36/539; A61K 36/487; A61K 47/36
USPC ................................. 424/439, 456
See application file for complete search history.

(56) References Cited

U.S. PATENT DOCUMENTS 2,954,293 A 9/1960 Rusoff
3,554,768 A 1/1971 Feldman
(Continued)

FOREIGN PATENT DOCUMENTS

AU 549614 B2 2/1986
CA 1162699 A 2/1984
(Continued)

OTHER PUBLICATIONS

Langrish, T., et al, "Spray drying of food ingredients and applications of CFD in spray drying", "Chemical Engineering and Processing", 2001, pp. 345-354, vol. 40.
(Continued)

*Primary Examiner* — Davis Hwu
(74) *Attorney, Agent, or Firm* — Hultquist, PLLC; Steven J. Hultquist

(57) ABSTRACT

Methods and apparatus provide for spray drying a liquid product into a dried powder without applying heat, including: forming a slurry including a liquid solvent, a carrier, and an active ingredient; applying an electrostatic charge to the slurry; atomizing the charged slurry to produce a plurality of electrostatically charged, wet particles; suspending the electrostatically charged, wet particles for a sufficient time to permit repulsive forces induced by the electrostatic charge on at least some wet particles to cause at least some of such particles to divide into wet sub-particles; and continuing the suspending step, without the presence of any heated drying fluids, for a sufficient time to drive off a sufficient amount of the liquid solvent within most of the wet particles to leave a plurality of dried particles (the powder), each dried particle containing the active ingredient encapsulated within the carrier.

20 Claims, 17 Drawing Sheets

(51) Int. Cl.
*A61K 9/16* (2006.01)
*C11B 9/00* (2006.01)
*A23L 1/00* (2006.01)

(56) References Cited

U.S. PATENT DOCUMENTS

| | | | |
|---|---|---|---|
| 3,615,723 A | 10/1971 | Meade et al. |
| 3,655,397 A | 4/1972 | Parliment et al. |
| 3,677,321 A | 7/1972 | Felstead |
| 3,679,416 A | 7/1972 | Reich |
| 3,741,273 A | 6/1973 | Meade |
| 3,805,869 A | 4/1974 | Winter et al. |
| 3,817,308 A | 6/1974 | Bundo |
| 3,840,996 A | 10/1974 | Grindstaff et al. |
| 3,844,969 A | 10/1974 | Griffiths et al. |
| 3,886,297 A | 5/1975 | Parliment et al. |
| 3,920,815 A | 11/1975 | Harvey et al. |
| 3,956,521 A | 5/1976 | Pisecky et al. |
| 3,962,321 A | 6/1976 | Parliment et al. |
| 3,962,384 A | 6/1976 | Cannalonga et al. |
| 3,963,559 A | 6/1976 | Petersen et al. |
| 3,966,975 A | 6/1976 | Hansen et al. |
| 4,001,437 A | 1/1977 | Jaeggi et al. |
| 4,032,465 A | 6/1977 | Bauer et al. |
| 4,062,641 A | 12/1977 | Hovmand et al. |
| 4,070,766 A | 1/1978 | Kamphuis |
| 4,072,570 A | 2/1978 | Williams |
| 4,099,982 A | 7/1978 | Hansen et al. |
| 4,141,783 A | 2/1979 | Pisecky et al. |
| 4,198,308 A | 4/1980 | Micciche |
| 4,261,793 A | 4/1981 | Nakamura et al. |
| 4,276,312 A | 6/1981 | Merritt |
| 4,281,024 A | 7/1981 | Hauberg et al. |
| 4,302,481 A | 11/1981 | Ribnitz et al. |
| 4,362,273 A | 12/1982 | Seino et al. |
| 4,420,442 A | 12/1983 | Sands |
| 4,422,900 A | 12/1983 | Bordelon et al. |
| 4,438,147 A | 3/1984 | Hedrick, Jr. |
| 4,476,042 A | 10/1984 | Sprecker et al. |
| 4,476,147 A | 10/1984 | Hall et al. |
| 4,481,221 A | 11/1984 | Mookherjee et al. |
| 4,481,224 A | 11/1984 | Muralidhara et al. |
| 4,490,403 A | 12/1984 | Pisecky et al. |
| 4,511,592 A | 4/1985 | Percel et al. |
| 4,515,987 A | 5/1985 | Boden et al. |
| 4,520,032 A | 5/1985 | Hall et al. |
| 4,521,613 A | 6/1985 | Pittet et al. |
| 4,521,634 A | 6/1985 | Fujioka et al. |
| 4,522,765 A | 6/1985 | Wiegers et al. |
| 4,524,010 A | 6/1985 | Reuter et al. |
| 4,525,364 A | 6/1985 | Wiegers et al. |
| 4,532,145 A | 7/1985 | Saleeb et al. |
| 4,532,364 A | 7/1985 | Fujioka et al. |
| 4,535,192 A | 8/1985 | Hall et al. |
| 4,537,704 A | 8/1985 | Sprecker et al. |
| 4,539,143 A | 9/1985 | Boden et al. |
| 4,539,209 A | 9/1985 | Wilson et al. |
| 4,544,775 A | 10/1985 | Fujioka et al. |
| 4,548,821 A | 10/1985 | Hall et al. |
| 4,552,770 A | 11/1985 | Pittet et al. |
| 4,565,707 A | 1/1986 | Pittet et al. |
| 4,568,538 A | 2/1986 | Boden et al. |
| 4,571,344 A | 2/1986 | Pittet et al. |
| 4,600,576 A | 7/1986 | Pittet et al. |
| 4,613,511 A | 9/1986 | Pittet et al. |
| 4,614,831 A | 9/1986 | Sprecker et al. |
| 4,619,780 A | 10/1986 | Fujioka et al. |
| 4,620,945 A | 11/1986 | Mookherjee et al. |
| 4,623,538 A | 11/1986 | Pittet et al. |
| 4,623,547 A | 11/1986 | Pittet et al. |
| 4,626,440 A | 12/1986 | Pittet et al. |
| 4,629,586 A | 12/1986 | Wilson et al. |
| 4,629,805 A | 12/1986 | Sprecker et al. |
| 4,632,831 A | 12/1986 | Hall |
| 4,643,903 A | 2/1987 | Sprecker et al. |
| 4,661,281 A | 4/1987 | Seiter et al. |
| 4,677,207 A | 6/1987 | Boden et al. |
| 4,679,733 A | 7/1987 | Lipp |
| 4,680,142 A | 7/1987 | Pittet et al. |
| 4,681,976 A | 7/1987 | Sprecker et al. |
| 4,724,121 A | 2/1988 | Weyand |
| 4,762,636 A | 8/1988 | Balliello et al. |
| 4,794,193 A | 12/1988 | Pittet et al. |
| 4,804,496 A | 2/1989 | Lowery et al. |
| 4,840,801 A | 6/1989 | Mookherjee et al. |
| 4,849,125 A | 7/1989 | Seiter et al. |
| 4,865,853 A | 9/1989 | Mookherjee et al. |
| 4,873,112 A | 10/1989 | Mitchell et al. |
| 4,883,884 A | 11/1989 | Boden et al. |
| 4,892,910 A | 1/1990 | Klesse et al. |
| 4,931,203 A | 6/1990 | Ahmed et al. |
| 4,936,901 A | 6/1990 | Surgant et al. |
| 4,950,495 A | 8/1990 | Boden et al. |
| 4,962,089 A | 10/1990 | Boden et al. |
| 4,983,579 A | 1/1991 | Boden et al. |
| 5,004,618 A | 4/1991 | Buckholz, Jr. et al. |
| 5,094,860 A | 3/1992 | Newhall et al. |
| 5,100,509 A | 3/1992 | Pisecky et al. |
| 5,124,162 A | 6/1992 | Boskovic et al. |
| 5,130,149 A | 7/1992 | Keller et al. |
| 5,137,741 A | 8/1992 | Zampino et al. |
| 5,153,011 A | 10/1992 | Patel et al. |
| 5,196,219 A | 3/1993 | Hsu et al. |
| 5,227,017 A | 7/1993 | Tanaka et al. |
| 5,338,553 A | 8/1994 | Johnson et al. |
| 5,354,742 A | 10/1994 | Deming et al. |
| 5,391,647 A | 2/1995 | Yamamoto et al. |
| 5,443,829 A | 8/1995 | Kensil et al. |
| 5,445,839 A | 8/1995 | Hagiwara et al. |
| 5,462,978 A | 10/1995 | Penzel et al. |
| 5,506,353 A | 4/1996 | Subramaniam |
| 5,525,367 A | 6/1996 | King et al. |
| 5,593,715 A | 1/1997 | Christensen |
| 5,702,749 A | 12/1997 | Sugiura et al. |
| 5,723,424 A * | 3/1998 | Jennings ............ C11D 11/0052 134/42 |
| 5,759,599 A | 6/1998 | Wampler et al. |
| 5,773,061 A | 6/1998 | Getler et al. |
| 5,786,017 A | 7/1998 | Blake et al. |
| 5,840,360 A | 11/1998 | Larsen |
| 5,891,473 A | 4/1999 | Stanier |
| 5,968,575 A | 10/1999 | Rasmussen |
| 6,048,565 A | 4/2000 | Getler et al. |
| 6,058,624 A | 5/2000 | Bach et al. |
| 6,077,543 A | 6/2000 | Gordon et al. |
| 6,200,949 B1 | 3/2001 | Reijmer et al. |
| 6,251,463 B1 | 6/2001 | Rossy et al. |
| 6,253,463 B1 | 7/2001 | Hansen |
| 6,325,859 B1 | 12/2001 | De Roos et al. |
| 6,335,045 B1 | 1/2002 | Peters et al. |
| 6,387,431 B1 | 5/2002 | Gautschi |
| 6,391,361 B1 | 5/2002 | Peters et al. |
| RE37,860 E | 9/2002 | Blake et al. |
| 6,474,573 B1 | 11/2002 | Kelly |
| 6,482,433 B1 | 11/2002 | DeRoos et al. |
| 6,497,911 B1 | 12/2002 | Hansen et al. |
| 6,560,897 B2 | 5/2003 | Chickering et al. |
| 6,582,728 B1 | 6/2003 | Platz et al. |
| 6,607,771 B2 | 8/2003 | Benczedi et al. |
| 6,607,778 B2 | 8/2003 | Mutka et al. |
| 6,649,267 B2 | 11/2003 | Agawa et al. |
| 6,652,898 B2 | 11/2003 | Jensen |
| 6,656,394 B2 | 12/2003 | Kelly |
| 6,689,755 B1 | 2/2004 | Gabel et al. |
| 6,723,359 B2 | 4/2004 | Subramaniam et al. |
| 6,734,158 B2 | 5/2004 | Starkenmann |
| 6,763,607 B2 | 7/2004 | Beyerinck et al. |
| 6,769,200 B2 | 8/2004 | Raehse et al. |
| 6,838,100 B2 | 1/2005 | Jaeger et al. |
| 6,902,751 B1 | 6/2005 | Schleifenbaum et al. |
| 6,929,814 B2 | 8/2005 | Bouwmeesters et al. |
| 6,933,265 B2 | 8/2005 | Marty |
| 6,962,006 B2 | 11/2005 | Chickering, III et al. |
| 6,964,385 B2 | 11/2005 | Kelly |

(56) References Cited

U.S. PATENT DOCUMENTS

| | | | |
|---|---|---|---|
| 7,022,665 B2 | 4/2006 | Decorzant et al. | |
| 7,090,832 B2 | 8/2006 | Zanone et al. | |
| 7,097,872 B2 | 8/2006 | Dewis et al. | |
| 7,128,936 B1 | 10/2006 | Hansen | |
| 7,176,176 B2 | 2/2007 | Pickenhagen et al. | |
| 7,176,177 B2 | 2/2007 | Lambrecht et al. | |
| 7,204,998 B2 | 4/2007 | Holzner et al. | |
| 7,252,848 B2 | 8/2007 | Gelin | |
| 7,316,826 B2 | 1/2008 | Kindel et al. | |
| 7,332,468 B2 | 2/2008 | Widder et al. | |
| 7,348,035 B2 | 3/2008 | Schleifenbaum et al. | |
| 7,361,376 B2 | 4/2008 | Dewis et al. | |
| 7,378,121 B2 | 5/2008 | Ley et al. | |
| 7,534,460 B2 | 5/2009 | Dewis et al. | |
| 7,651,713 B2 | 1/2010 | Keller | |
| 8,939,388 B1 * | 1/2015 | Beetz | F26B 3/12 239/690 |
| 2002/0187221 A1 | 12/2002 | Tanaka et al. | |
| 2003/0003212 A1 | 1/2003 | Chien et al. | |
| 2003/0021883 A1 | 1/2003 | Skiff | |
| 2003/0082272 A1 | 5/2003 | Bouwmeesters et al. | |
| 2003/0192815 A1 | 10/2003 | Kelly | |
| 2003/0196957 A1 | 10/2003 | Henningfield et al. | |
| 2003/0205629 A1 | 11/2003 | Kelly | |
| 2004/0062845 A1 | 4/2004 | Krawczyk et al. | |
| 2004/0253343 A1 | 12/2004 | Ha et al. | |
| 2005/0031769 A1 | 2/2005 | Watanabe et al. | |
| 2005/0209443 A1 | 9/2005 | Bolen et al. | |
| 2005/0282728 A1 | 12/2005 | Narula et al. | |
| 2006/0035008 A1 | 2/2006 | Virgallito et al. | |
| 2006/0159818 A1 | 7/2006 | Kunieda | |
| 2006/0264130 A1 | 11/2006 | Karles et al. | |
| 2007/0054837 A1 | 3/2007 | Weiss et al. | |
| 2007/0078071 A1 | 4/2007 | Lee et al. | |
| 2007/0117727 A1 | 5/2007 | Narula et al. | |
| 2007/0166185 A1 | 7/2007 | Bartels | |
| 2007/0184163 A1 | 8/2007 | Toth et al. | |
| 2007/0218179 A1 | 9/2007 | Ott et al. | |
| 2007/0231424 A1 | 10/2007 | Castro et al. | |
| 2007/0297993 A1 | 12/2007 | Kindel et al. | |
| 2008/0008801 A1 | 1/2008 | Barnekow et al. | |
| 2008/0015264 A1 | 1/2008 | Schleifenbaum et al. | |
| 2008/0057175 A1 | 3/2008 | Barnekow et al. | |
| 2008/0063747 A1 | 3/2008 | Boghani et al. | |
| 2008/0064625 A1 | 3/2008 | Holscher | |
| 2008/0081779 A1 | 4/2008 | Holscher | |
| 2008/0107786 A1 | 5/2008 | Barnekow et al. | |
| 2008/0113073 A1 | 5/2008 | Ley et al. | |
| 2008/0199592 A1 | 8/2008 | Fexer et al. | |
| 2008/0214675 A1 | 9/2008 | Ley et al. | |
| 2008/0220140 A1 | 9/2008 | Ley et al. | |
| 2008/0227866 A1 | 9/2008 | Ley et al. | |
| 2008/0241322 A1 | 10/2008 | Bunge | |
| 2008/0242585 A1 | 10/2008 | Ott et al. | |
| 2008/0242740 A1 | 10/2008 | Ley et al. | |
| 2008/0292763 A1 | 11/2008 | Looft et al. | |
| 2008/0305052 A1 | 12/2008 | Ley et al. | |
| 2008/0317923 A1 | 12/2008 | Ley et al. | |
| 2009/0081140 A1 | 3/2009 | Brocke et al. | |
| 2009/0091049 A1 | 4/2009 | Nielsen | |
| 2009/0092725 A1 | 4/2009 | Panten et al. | |
| 2009/0110796 A1 | 4/2009 | Backes et al. | |
| 2009/0124701 A1 | 5/2009 | Langer et al. | |
| 2009/0155445 A1 | 6/2009 | Le et al. | |
| 2009/0155446 A1 | 6/2009 | Reiss et al. | |
| 2009/0163403 A1 | 6/2009 | Levorse, Jr. et al. | |
| 2009/0163404 A1 | 6/2009 | Levorse, Jr. et al. | |
| 2009/0252789 A1 | 10/2009 | Trophardy | |
| 2009/0291176 A1 | 11/2009 | Nagao et al. | |
| 2010/0055267 A1 | 3/2010 | Popplewell et al. | |
| 2010/0196493 A1 | 8/2010 | Buisson | |
| 2011/0059205 A1 | 3/2011 | Gaysinsky et al. | |
| 2011/0064783 A1 | 3/2011 | Bang-Madsen et al. | |
| 2013/0022728 A1 | 1/2013 | Popplewell et al. | |
| 2014/0193562 A1 | 7/2014 | Popplewell et al. | |
| 2014/0205713 A1 | 7/2014 | Hans et al. | |

FOREIGN PATENT DOCUMENTS

| | | |
|---|---|---|
| CA | 1334460 C | 3/1989 |
| CA | 1314432 C | 3/1993 |
| CA | 2171389 C | 3/1996 |
| CA | 2258751 C | 12/1997 |
| CA | 2253154 C | 5/1999 |
| CA | 2321660 C | 9/1999 |
| CA | 2407614 C | 11/2001 |
| CA | 2663386 A1 | 4/2008 |
| EP | 0322137 A1 | 6/1989 |
| EP | 0344375 B1 | 12/1989 |
| EP | 0232313 B1 | 5/1990 |
| EP | 0180366 B1 | 6/1990 |
| EP | 0420509 A1 | 4/1991 |
| EP | 0227486 B1 | 11/1991 |
| EP | 0515478 B1 | 12/1993 |
| EP | 0429482 B1 | 4/1994 |
| EP | 0461197 B1 | 6/1994 |
| EP | 0517423 B1 | 3/1995 |
| EP | 0366898 B1 | 2/1996 |
| EP | 0619075 B1 | 1/1997 |
| EP | 0832695 A2 | 4/1998 |
| EP | 1064856 A2 | 1/2001 |
| EP | 1106081 A1 | 6/2001 |
| EP | 1280591 B1 | 12/2006 |
| EP | 1435797 B1 | 8/2007 |
| EP | 2052622 A1 | 4/2009 |
| EP | 2138567 A1 | 12/2009 |
| GB | 575118 A | 2/1946 |
| GB | 1015599 A | 1/1966 |
| GB | 2364714 A | 2/2002 |
| IE | 62024 B1 | 12/1994 |
| WO | 9117821 A1 | 11/1991 |
| WO | 9428181 A2 | 12/1994 |
| WO | 9513864 A1 | 5/1995 |
| WO | 9517174 A1 | 6/1995 |
| WO | 9713416 A1 | 4/1997 |
| WO | 9714288 A2 | 4/1997 |
| WO | 9733485 A1 | 9/1997 |
| WO | 9804243 A1 | 2/1998 |
| WO | 0167897 A1 | 9/2001 |
| WO | 0207541 A1 | 1/2002 |
| WO | 2005063032 A1 | 7/2005 |
| WO | 2006082536 A1 | 8/2006 |
| WO | 2007054853 A1 | 5/2007 |
| WO | 2007096790 A1 | 8/2007 |
| WO | 2007135583 A2 | 11/2007 |
| WO | 2008047301 A1 | 4/2008 |
| WO | 2008077399 A1 | 7/2008 |
| WO | 2008113778 A1 | 9/2008 |
| WO | 2010104713 A1 | 9/2010 |
| WO | 2011121468 A1 | 10/2011 |
| WO | 2012122010 A2 | 9/2012 |

OTHER PUBLICATIONS

Leuenberger, H., "Spray freeze-drying—the process of choice for low water soluble drugs?", "Journal of Nanoparticle Research", 2002, pp. 111-119, vol. 4.

Moeller, J., et al., "A Primer on Spray Drying", "Chemical Engineering", Nov. 2009, pp. 34-40.

Mumenthaler, M., et al., "Atmospheric spray-freeze drying: a suitable alternative in freeze-drying technology", "International Journal of Pharmaceutics", 1991, pp. 97-110, vol. 72.

Rayleigh, L., "XX. On the Equilibrium of Liquid Conducting Masses Charged With Electricity", "Philosophical Magazine Series 5", 1882, pp. 184-186, vol. 14, No. 87.

Sirignano, W., "Fluid Dynamics and Transport of Droplets and Sprays, Second Edition", Jan. 2010, p. 34 Publisher: Cambridge University Press.

Westergaard, V., "The New Niro Integrated Filter Dryer IFD", "Danish Dairy and Food Industry . . . worldwide", Sep. 2002, pp. 62-64.

(56) References Cited

OTHER PUBLICATIONS

Bailey, A., "Electrostatic Spraying of Liquids", Apr. 1988, pp. 1-35, Publisher: Research Studies Press Ltd., Published in: Taunton, Somerset, England.

Broadhead, J., et al., "The Spray Drying of Pharmaceuticals", "Drug Development and Industrial Pharmacy", 1992, pp. 1169-1206, vol. 18, No. 11 and 12.

Coumans, W., et al., "Theoretical and Practical Aspects of Aroma Retention in Spray Drying and Freeze Drying", "Drying Technology", 1994, pp. 99-149, vol. 12, No. 1 and 2.

Dobry, D., et al., "A Model-Based Methodology for Spray-Drying Process Development", "J. Pharm. Innov.", Jul. 25, 2009, pp. 133-142, vol. 4.

GEA Processing Engineering, Inc., "GEA Powder Technology Division: Niro: Spray Drying", "Accessed via http://www.niroinc.com/html/drying/fdpdfs/480gbspraydrying.pdf", Aug. 22, 2002, pp. 1-15.

Gohel, M., et al., "Spray Drying: A Review", "Pharmaceutical Reviews", Sep. 28, 2009, pp. 1-20, vol. 7, No. 5.

Gomez, A., et al., "Charge and fission of droplets in electrostatic sprays", "Phys. Fluids", Jan. 1994, pp. 404-414, vol. 6, No. 1.

Goula, A., et al., "Spray Drying of Tomato Pulp: Effect of Feed Concentration", "Drying Technology", 2004, pp. 2309-2330, vol. 22, No. 10.

Killeen, M., "The Process of Spray Drying and Spray Congealing", "Pharmaceutical Engineering", Jul./Aug. 1993, pp. 56, 58-62, 64, vol. 13.

\* cited by examiner

100

METHODS AND APPARATUS FOR LOW HEAT SPRAY DRYING

CROSS-REFERENCE TO RELATED APPLICATIONS

This is a continuation-in-part under 35 USC 120 of U.S. patent application Ser. No. 13/245,369 filed Sep. 26, 2011 in the names of Charles P. Beetz, Robert Corbett, and David Salem for "METHODS AND APPRATUS FOR LOW HEAT SPRAY DRYING," and issued Jan. 27, 2015 as U.S. Pat. No. 8,939,388, which in turn claims the benefit under 35 USC 119 of U.S. Provisional Patent Application No. 61/386,762, filed Sep. 27, 2010 in the names of Charles P. Beetz, Robert Corbett, and David Salem for "METHODS AND APPRATUS FOR LOW HEAT SPRAY DRYING." The disclosures of U.S. patent application Ser. No. 13/245,369 and U.S. Provisional Patent Application No. 61/386,762 are hereby incorporated herein by reference in their respective entireties, for all purposes.

FIELD

The present disclosure relates to methods and apparatus for spray drying a liquid product into a dried powder without applying heat, or applying substantially low amounts of heat.

DESCRIPTION OF THE RELATED ART

Spray drying is a method of producing a dry powder from a liquid or slurry by rapidly drying with a hot gas (usually air). Spray drying technology has existed since the late 1800's and has continually evolved over the past century.

The spray drying process begins with a liquid solvent, commonly water, containing dissolved or suspended components such as an emulsion. The suspension includes a substance to be encapsulated (the load) and an amphipathic carrier (usually some sort of modified starch), which are homogenized as a suspension in the liquid solvent. The load is typically some constituent component(s) of a food, fragrance, medicament, etc., and the homogenized suspension is often referred to as a slurry.

Spray dryers use some type of atomizer, such as a spray nozzle, to disperse the slurry into a controlled spray having some relatively controlled droplet size. Depending on the process requirements, droplet sizes may range from about 10 to 500 microns in diameter. The most common applications require droplet sizes in the 50 to 200 micron range.

In conjunction with atomization, the slurry is fed into a drying chamber, usually a tower into which heated air is also introduced. The temperature of the air as it enters the drying chamber is well over the boiling point of water, usually in the range of 180-200° C. The heated air supplies energy for evaporation of volatile components of the liquid (the water) from the droplets. As the water evaporates, the carrier forms a hardened shell around the load, producing a dried powder.

Reference is made to FIG. 1, which illustrates a conventional spray drying system 50 and associated process. The process begins with making a slurry of ingredients. The ingredients include a liquid solvent, such as water 1, a carrier 2, and active ingredient(s) 3. In the typical process, the water 1 and carrier 2 are added into the solution tank 4 while stirring. The active ingredient 3 is then added to the tank 4 and stirred into the slurry. The active ingredient is either emulsified in the carrier fluid system or dissolved into it. In order for conventional spray drying processes to be commercially viable, typical slurry viscosities must be in the range of about 10-300 mPa-s.

The slurry formed in the solution tank 4 is delivered to an atomizer 6 using a feed pump 5 or other means of conveyance. The slurry enters the atomizer 6 and leaves the atomizer as a spray of liquid droplets 8, and the droplets 8 are introduced into a drying chamber 7. Concurrently, a feed of air is heated by a process heater 11 and supplied into the drying chamber 7 by a blower 10. The water evaporated from the droplets 8 enters the heated air as the atomized liquid droplets 8 dry to form solid particles after exposure to the incoming heated air.

The dried powder leaves the dryer chamber 7 along with the water vapor laden air, and is carried to a cyclone separator 12, which removes the dried particles from the circulating air stream and deposits the particles into a collection container 13. The water vapor laden air exits the collection container 13 and enters a baghouse 14, where very fine particles are removed before the water vapor laden air is sent into a condenser 9, via blower 15. The condenser 9 removes the water vapor from the process air, and the collected water may be re-used or discarded.

One of the prominent attributes of the traditional spray drying process is the high temperature of the inlet gas (typically on the order of 200° C.) leaving the heater 11 and entering the drying chamber 7, as well as the temperature of the outlet gas exiting the drying chamber 7, which is usually in excess of 100° C. Although the liquid droplets 8 are injected into the high temperature environment within the chamber 7, the droplets 8 do not actually reach the inlet gas temperature. The droplets 8, however, do become heated to a point at which considerable portions of desired constituents of the droplets (i.e., portions of the load) are undesirably modified, such as evaporated and/or oxidized. The undesirable modification to the load (load loss) leads to a reduction in flavor (in the case of food loads), a reduction in aroma (in the case of fragrances), etc. Essentially, evaporation and heat degradation of the load lowers the performance characteristics of the final powder product, and therefore results in a significant degradation of performance in commercial use and a significant loss of revenue.

The above disadvantageous characteristics of the conventional spray dry process have resulted in many process modifications and emulsion formulations to compensate for heat induced alterations in the load. This is especially true in the pharmaceutical industry, where excessive heating during spray drying leads to degradation of the active ingredient in a powdered medicament. This also presents a challenge to flavorists in the powdered flavor industry to design flavor formulations that can survive the drying process and deliver acceptable (although significantly flawed) flavor characteristics.

In view of the above, there are needs in the art for new methods and apparatus for carrying out the spray drying process, which reduce or eliminate the disadvantageous characteristics of the conventional spray dry process.

SUMMARY

Methods and apparatus for spray drying a liquid product into a dried powder without applying heat provide for: forming a slurry including a liquid solvent, a carrier, and an active ingredient; applying an electrostatic charge to the slurry; atomizing the charged slurry to produce a plurality of electrostatically charged, wet particles; suspending the electrostatically charged, wet particles for a sufficient time to permit repulsive forces induced by the electrostatic charge on at least some wet particles to cause at least some of such particles to divide into wet sub-particles; and continuing the suspending step, without the presence of any heated drying fluids, for a sufficient time to drive off a sufficient amount of the liquid solvent within most of the wet particles to leave a plurality of dried particles (the powder), each dried particle containing the active ingredient encapsulated within the carrier.

Preferably, a temperature of the non-heated drying fluid is less than about 100° C. at introduction into the drying chamber, such as at least one of: less than about 75° C. at introduction into the drying chamber; less than about 45° C. at introduction into the drying chamber; less than about 35° C. at introduction into the drying chamber; less than about 30° C. at introduction into the drying chamber; and at about an ambient temperature of a room within which the drying chamber is located.

The methods and apparatus may further provide for subjecting the electrostatically charged, wet particles to a non-heated drying fluid within a drying chamber to drive off the liquid solvent. Alternatively or additionally, the methods and apparatus may further provide for dehumidifying the non-heated drying fluid prior to introduction into the drying chamber. Alternatively or additionally, the methods and apparatus may further provide for applying one or more electric fields within the drying chamber to urge at least one of the wet particles and the dry particles to travel in a direction defined from an inlet end of the drying chamber to an outlet end of the drying chamber.

The methods and apparatus may further provide for controlling one or more of a viscosity of the slurry during formation a ratio of water within the slurry during formation, such that one or more of: (i) the viscosity of the slurry at the atomization step is at least one of: greater than about 300 mPa-s; greater than about 350 mPa-s; greater than about 400 mPa-s; greater than about 500 mPa-s; greater than about 600 mPa-s; greater than about 700 mPa-s; between about 500-16,000 mPa-s; and between about 1000-4000 mPa-s; and (ii) the ratio of water within the slurry at the atomization step is at least one of: between about 20-50 weight percentage; between about 20-45 weight percentage; between about 20-45 weight percentage; between about 20-40 weight percentage; about 30 weight percentage.

The apparatus may include a drying chamber, including an inlet end, an outlet end, and an internal volume within which the liquid product is dried, where the drying chamber is formed from a non-electrically conductive material.

Additionally or alternatively, a first electrode may be located at or near the inlet end of the drying chamber; and a second electrode may be located at or near the outlet end of the drying chamber, where application of a source of voltage potential between the first and second electrodes induces an electric field within the drying chamber sufficient to urge particles of the liquid product, produced by way of atomization, from the inlet end toward the outlet end of the drying chamber. Preferably, the first and second electrodes are disposed external to the drying chamber, yet induce an electric field within the internal volume of the drying chamber by virtue of the formation of the drying chamber from the non-electrically conductive material.

The apparatus may additionally or alternatively include a nozzle operating to atomize a slurry to produce a plurality of wet particles, where the slurry includes a liquid solvent, a carrier, and an active ingredient. The apparatus may further include at least one electrode operating to contact the slurry and apply an electrostatic charge thereto, such that the nozzle operates to produce a plurality of electrostatically charged wet particles. The at least one electrode may be disposed within the nozzle such that the slurry contacts the electrode and becomes electrostatically charged while flowing from an inlet end to an outlet end of the nozzle.

A dried powder produced using one or more aspects of the invention may include: a plurality of dried particles, which individually contain an amount of final active ingredient encapsulated within a carrier resulting from drying a slurry containing an initial active ingredient, a liquid solvent and the carrier, wherein: the initial active ingredient includes one or more constituent components, at least one of which is among one or more principle molecular types from which at least one of a desirable food, flavor, fragrance, medicament, and pigment is obtained; the final active ingredient includes one or more of the constituent components corresponding with those of the initial active ingredient as modified by the drying of the slurry; and wherein a weight percentage of at least one of the one or more principle molecular types in the final active ingredient is within about 5% of a weight percentage of the corresponding principle molecular types in the initial active ingredient.

Alternatively or additionally, the weight percentage of at least one of the one or more principle molecular types in the final active ingredient may be within about 3%, 2% or 1% of a weight percentage of the corresponding principle molecular types in the initial active ingredient.

Additionally or alternatively, a dried powder produced using one or more aspects of the invention may include: a plurality of dried particles, which individually contain an amount of active ingredient encapsulated within a carrier, wherein: the active ingredient includes one or more constituent components, at least one of which is among one or more principle molecular types from which at least one of a desirable food, flavor, fragrance, medicament, and pigment is obtained; and wherein a weight percentage of at least one of the one or more principle molecular types in the active ingredient does not vary by more than about 5% during aging of the dried powder during any period of elevated temperature of about 95° F. up to about 1000 hours.

Additionally or alternatively, the weight percentage of at least one of the one or more principle molecular types in the active ingredient does not vary by more than about 3%, 2% or 1% during aging of the dried during any period of elevated temperature of about 95° F. up to about 1000 hours.

Other aspects, features, and advantages of the present invention will be apparent to one skilled in the art from the description herein taken in conjunction with the accompanying drawings.

BRIEF DESCRIPTION OF THE DRAWINGS

For the purposes of illustration, there are forms shown in the drawings that are presently preferred, it being understood, however, that the invention is not limited to the precise arrangements and instrumentalities shown.

DETAILED DESCRIPTION

Figure 1:
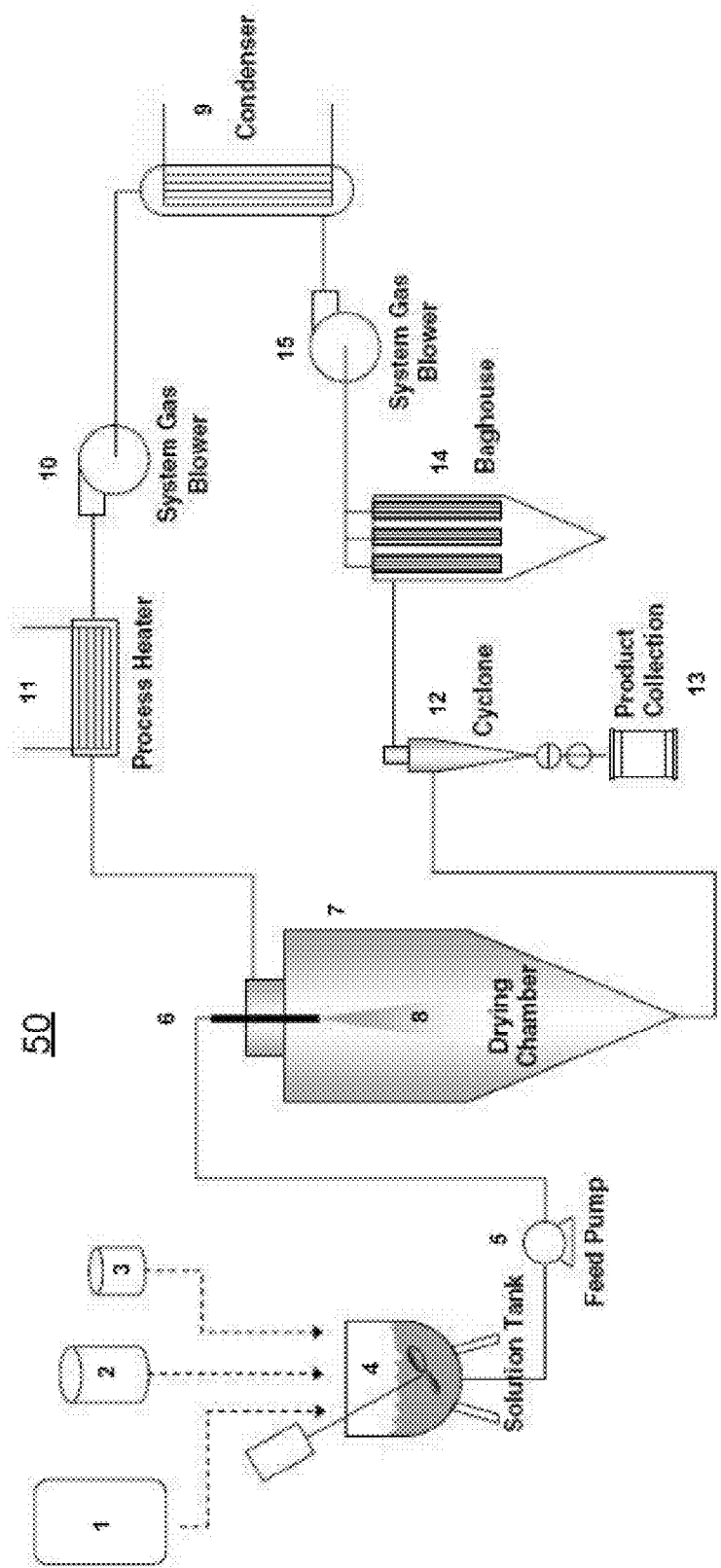
FIG. 1 is a system for spray drying a liquid product into a dried powder through the convention application of heated air in accordance with the prior art.

With reference to the drawings, wherein like numerals indicate like elements, there is shown in FIG. 2 a system 100 for spray drying a liquid product into a dried powder without employing heated air in accordance with one or more aspects of the present invention. The system 100 includes some of the same or similar elements as in the system 50 of FIG. 1, which elements have the same reference designators.

By way of a high level description, the system 100 includes a drying chamber 107 into which a slurry is fed by way of a feed pump 5 (or equivalent conveying mechanism). The slurry enters an atomizer 106 and leaves the atomizer as a spray of liquid droplets 108, which are introduced into the drying chamber 7. Concurrently, a feed of non-heated fluid (such as air or another suitable gas) is supplied into the drying chamber 107 by a blower 10. The supplied air may be subjected to dehumidification (via dehumidifier 110) prior to introduction into the drying chamber 107. The atomized liquid droplets 108 dry to form solid particles after exposure to the incoming air. Water evaporates from the droplets 108 and enters the air within the drying chamber 107. Dried powder leaves the drying chamber 107 along with the water vapor laden air, and is carried to a cyclone separator 12, which removes the dried particles from the circulating air stream and deposits the particles into a collection container 13. The water vapor laden air exits the collection container 13 and enters a baghouse 14, where very fine particles are removed before the water vapor laden air is sent into a condenser 9, via blower 15. The condenser 9 removes the water vapor from the process air, and the collected water may be re-used or discarded.

There are a number of very significant differences between the systems of FIGS. 1 and 2. Among these differences is the fact that the system 100 and related spray drying process does not use a heated fluid (e.g., air) to dry the atomized droplets within the drying chamber. The use of non-heated air is directly counter to the conventional and accepted wisdom in the spray drying art. Indeed, there is no known prior art spray drying process or system that does not use significantly heated air (on the order of 200° C.) in the drying process, despite the fact that the load loss associated with the heating process is well understood by skilled artisans. The reason that conventional spray drying processes call for heated air, however, is that artisans have failed to develop an alternative to using heated air that results in suitable (albeit degraded) dried powder product.

Among the reasons that non-heated air may be used in the spray drying system 100 and process is that the slurry is not conventional. In general, the slurry includes a liquid solvent, a carrier, and an active ingredient. The liquid solvent is usually water, however, other suitable solvents may be employed if needed or desired. The carrier is usually a modified starch. The active ingredient may be any desirable single constituent component or a combination of constituent components, at least one of which is among one or more principle molecular types from which at least one of a desirable food, flavor, fragrance, medicament, pigment, probiotic, bacteria, etc. is obtained.

Formation of the slurry is controlled such that regulation of at least one of the viscosity, the amount of liquid solvent (e.g., water), or other suitable metric relating to the water content of the slurry, is obtained. For example, the formation of the slurry may include controlling a viscosity of the slurry such that the viscosity at the atomization step is at least one of: greater than about 300 mPa-s; greater than about 350 mPa-s; greater than about 400 mPa-s; greater than about 500 mPa-s; greater than about 600 mPa-s; greater than about 700 mPa-s; between about 500-16,000 mPa-s; and between about 1000-4000 mPa-s. Additionally or alternatively, the formation of the slurry may include controlling a ratio of water within the slurry such that the ratio of water within the slurry at the atomization step is at least one of: between about 20-50 weight percentage; between about 20-45 weight percentage; between about 20-45 weight percentage; between about 20-40 weight percentage; and about 30 weight percentage. In order to provide some information as to the significant differences between a slurry according to one or more embodiments of the invention and conventional slurries, it is noted that conventional slurries have viscosities between about 10-200 mPa-s and contain an amount of water between about 50-70% by weight.

Another reason that non-heated air may be used in the spray drying system 100 (and process) relates to an unconventional electrostatic charging process that is conducted before, during or after atomization. In particular, an electrostatic charge is applied to the slurry or to the atomized droplets 108, preferably the former. In this regard, the system 100 includes a high voltage supply 104 (such as about 45 kV DC) that is coupled to one or more electrodes (not shown in FIG. 2). The polarity of the high voltage supply 104 may be in either the positive or negative configuration. The slurry (or atomized droplets 108) is brought into contact with the electrode to impart an electrical charge thereto. In a preferred embodiment, the slurry is brought into contact with the electrode(s) in order to produce a charged slurry. Concurrently or thereafter, the charged slurry is atomized to produce a plurality of electrostatically charged, wet particles (droplets) 108.

The respective charge on the wet droplets 108 produces a force that tends to cause adjacent droplets to repel one another. Additionally, the force on a given droplet 108 opposes the surface tension of such given droplet 108. When the charge on the given droplet 108 exceeds a threshold level, the Rayleigh limit, the droplet 108 becomes unstable and smaller satellite droplets 108 are ejected from the given (parent) droplet 108. One or more of the satellite droplets 108, in turn, might also become unstable and produce additional satellite droplets 108, since the surface charge density does not diminish in the satellite droplets 108 as evaporation takes place.

The electrostatically charged, wet particles/droplets 108 are suspended for a sufficient time within the drying chamber 107 to permit the aforementioned repulsive forces induced by the electrostatic charge on at least some wet particles/droplets 108 to cause at least some of such particles to divide into wet sub-particles/droplets 108. The suspension of the droplets 108 continues, without the presence of any heated drying fluids, for a sufficient time to drive off a sufficient amount of the liquid solvent within most of the wet particles/droplets 108 to leave a plurality of dried particles (the powder), each dried particle containing the active ingredient encapsulated within the carrier. Notably, the production of sub-particles/droplets 108 from a given volume of atomized slurry (i.e., from a given droplet 108) results in faster drying of such volume due to a greatly increased aggregate surface area of the sub-particles/droplets 108 and concomitant reduction of particle volume of each sub-particle/droplet 108 following each fission event.

The production of sub-particles/droplets 108 may be referred to as coulombic fission. The time scale for such coulombic fission events is on the order of a few microseconds to milliseconds. The fission of about ten (10) sub-particles/droplets 108 from a given particle/droplet 108 reduces a diameter of the given particle/droplet 108 by about 30%. The amount of time that it takes to achieve such reduction in diameter (on the order of a few microseconds to milliseconds) is an order of magnitude faster than diffusive evaporation in the presence of heated air, which occurs with a characteristic time t in accordance with the following formula:

$$t = do^2/k$$

where do is the diameter of the particle and k is the evaporative diffusion coefficient. For particles in the 20 to 200 mm diameter range, the time to any significant diameter reduction by evaporation is on the order of tenths to several seconds, which is far longer (one to two orders of magnitude) than diameter reduction by coulombic fission.

The individual or combined characteristics of relative low water content in the slurry and electrostatic charge on the droplets 108 permits vastly a different temperature condition within the drying chamber 107 as compared with prior art systems and processes. For example, a temperature of the non-heated drying fluid (air) introduced into the drying chamber 107 may be at least one of: less than about 100° C.; less than about 75° C.; less than about 45° C.; less than about 35° C.; less than about 30° C.; and at about an ambient temperature of a room within which the drying chamber 107 is located. The above temperature ranges assume a lower limit above freezing.

It has been demonstrated that an inlet air temperature of about 40° C. may result in an outlet air temperature of about 32° C. from the drying chamber 107.

While elevated temperatures as compared to the convention spray drying process of the prior art may not be necessary, it may be desirable to ensure that the drying fluid (air) introduced into the drying chamber 107 is of relatively low water content. Thus, the system 100 may include the process dehumidifier 110 in order to remove some amount of water from the air prior to introduction into the drying chamber 107. After dehumidification, the non-heated air as input into the drying chamber 107 may be at a relative humidity of about 7%.

The atomizer 106 may be implemented by way of any of the known methods, apparatus, and/or techniques. For example, the atomizer 106 may be implemented using at least one of: a nozzle technique, a centrifugal technique, a pneumatic technique, and an ultrasonic technique. For most atomization techniques, the slurry does not leave the atomizing mechanism as a final droplet 108, but rather as a fragment of a thin liquid film or ligament. The formation of droplets 108 takes place immediately after the liquid has left the atomizing mechanism, due to the surface tension of the liquid. The droplet size from a given type of atomization depends on the energy input into breaking the slurry into fragments, i.e., increasing the overall effective surface area of the slurry.

The average droplet size and distribution may be fairly constant for a given atomization technique, and may be in the range of 10-300 microns. The electrostatic charge process and resultant coulombic fission process in accordance with the various embodiments herein produces, in general, larger particles than conventional spray drying processes. The larger particles, however, come from even larger, parent particles, which conventional atomizers cannot adequately produce. The daughter particles produced in accordance with the embodiments herein are smaller, and the process tends to make bimodal size distributions for very viscous slurries.

Centrifugal (or rotary) atomization may be considered the most common form of atomization. Centrifugal atomization employs a rotating disc or wheel, which breaks the liquid stream of slurry into droplets. The centrifugal atomization device may employ a disc or wheel of about 5 to 50 cm in diameter, which spins in the range of about 5,000 to 40,000 rpm. The size of the droplets 108 produced by a centrifugal atomization device is about inversely proportional to the peripheral speed of the disc or wheel.

Nozzle atomization employs a pump (e.g., the feed pump 5 of FIG. 2), which pressurizes and forces the slurry through the orifice of a nozzle to break the liquid into fine droplets. The orifice size is usually in the range of 0.5 to 30 mm. The size of the droplets depends on the size of the orifice and the pressure drop. A larger pressure drop across the orifice produces smaller droplets. Therefore, to reduce the particle/droplet size for a given feed rate, a smaller orifice and a higher pump pressure may be employed.

Two-fluid pneumatic atomization employs the interaction of the slurry with another fluid, usually compressed air using a fluid nozzle for the compressed air and a fluid nozzle for the slurry. The pressure of the air and slurry may be in the range of about 200 to 350 kPa. Particle size is controlled by varying a ratio of the compressed air flow to that of the slurry flow.

Sonic atomization employs ultrasonic energy to vibrate a surface at ultrasonic frequencies. The slurry is brought into contact with the vibrating surface in order to produce the particles/droplets 108.

Figure 2:
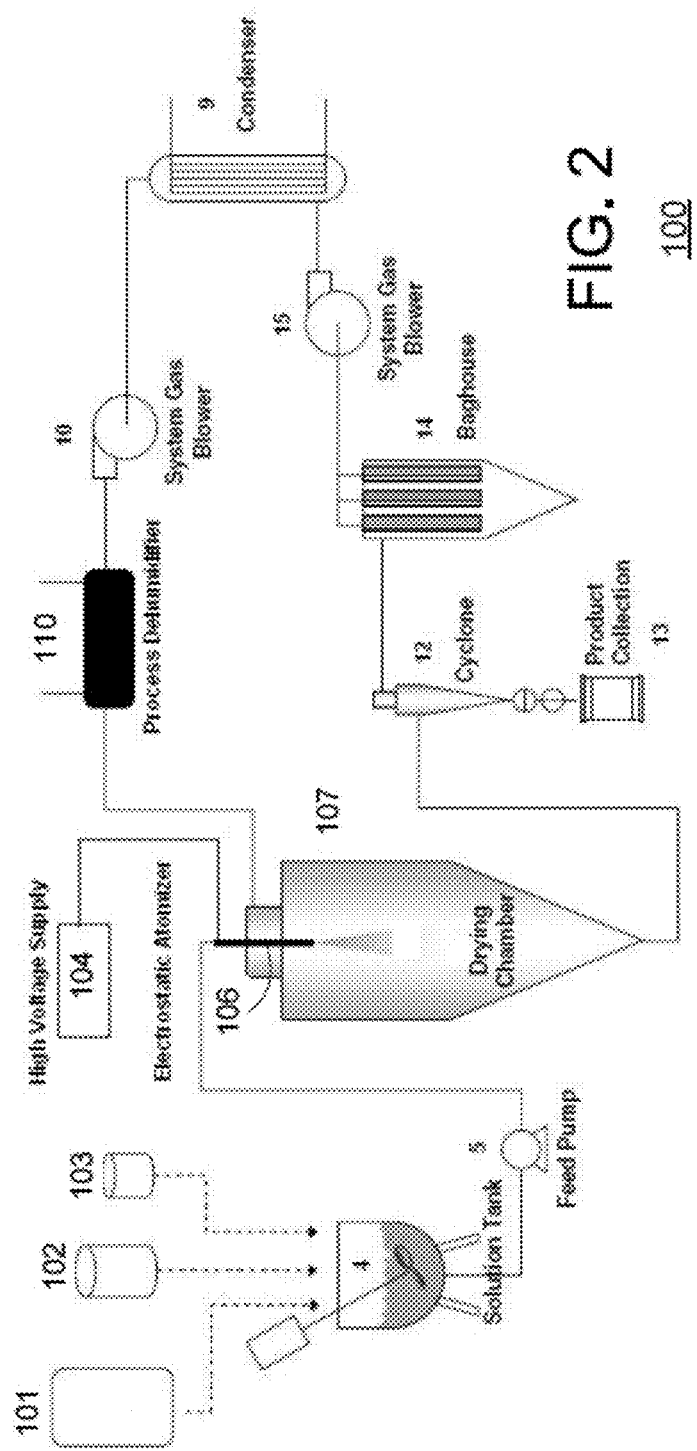
FIG. 2 is a system for spray drying a liquid product into a dried powder without employing heated air in accordance with one or more aspects of the present invention.
Figure 3:
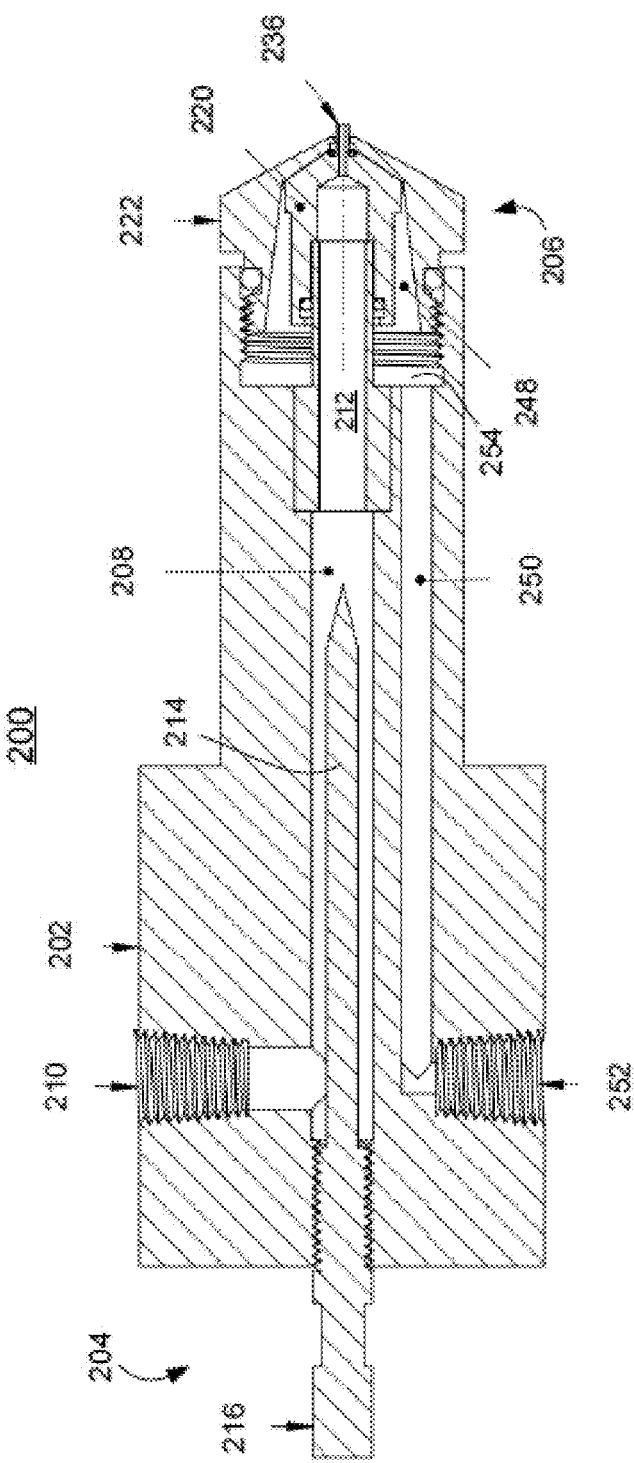
FIG. 3 is a cross-sectional view of an atomizer that may be employed in the system of FIG. 2 in order to produce a plurality of droplets from a slurry in accordance with one or more aspects of the present invention.
Figure 4:
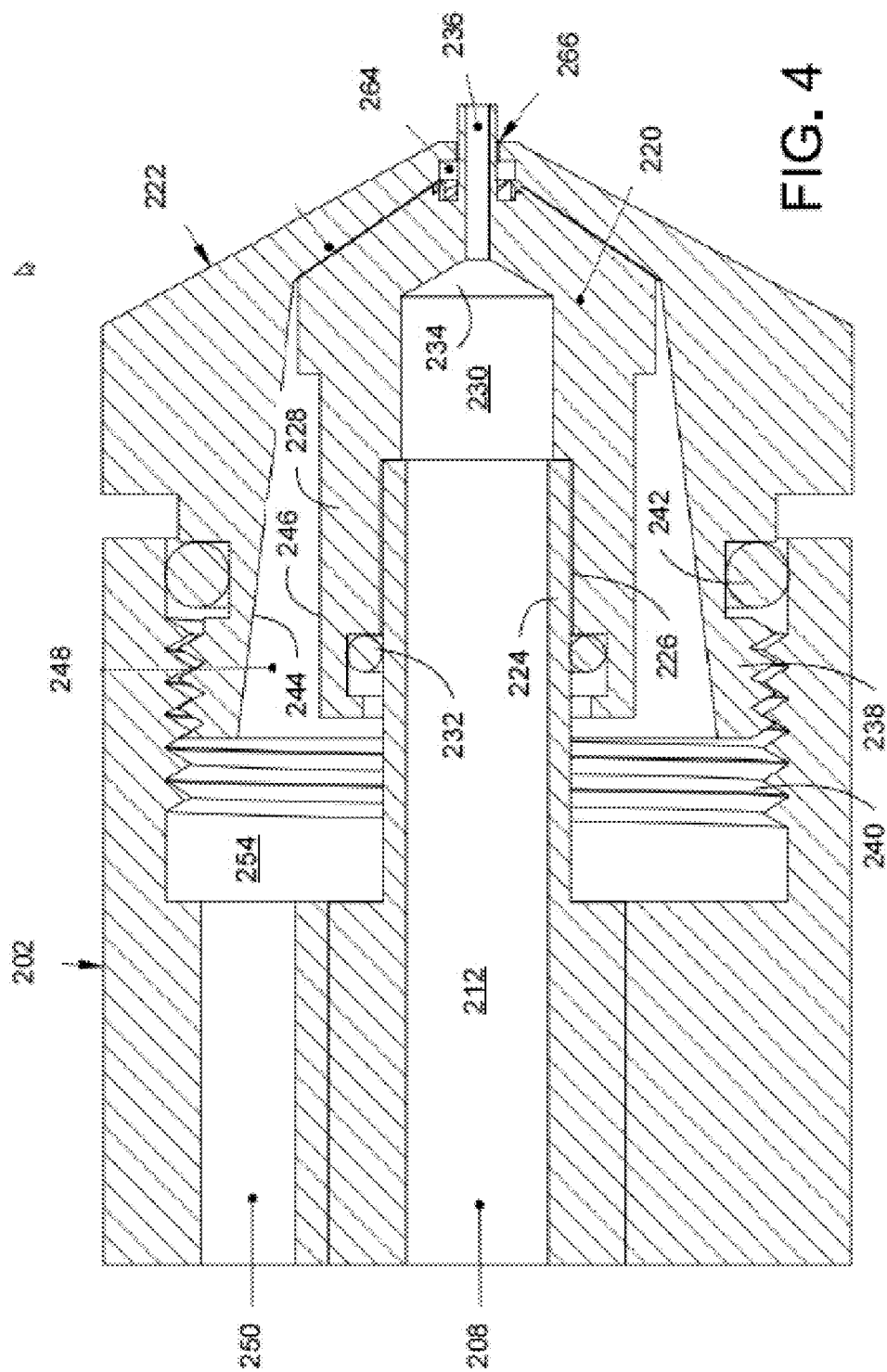
FIG. 4 is a cross-sectional view of a distal end of an atomizer that may be employed in the atomizer of FIG. 3 in accordance with one or more aspects of the present invention.
Figure 5:
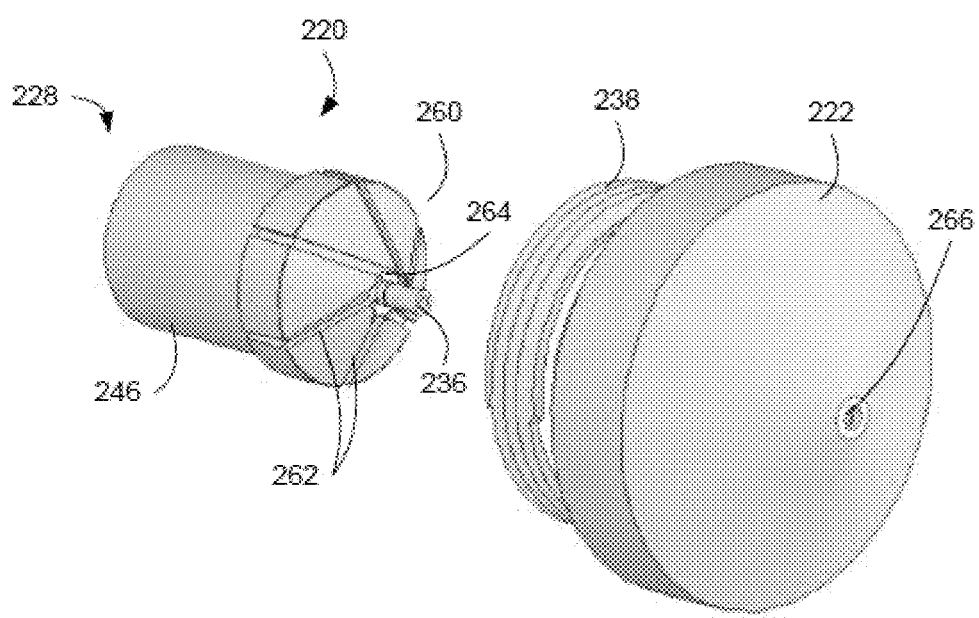
FIG. 5 is a perspective, exploded view of certain components of the distal end of the atomizer of FIG. 4 in accordance with one or more aspects of the present invention.

With reference to FIGS. 3-5, one or more embodiments of the present invention may employ a nozzle-type atomizer 106. FIG. 3 is a cross-sectional view of a two-fluid atomizer 200 that may be employed as the atomizer 106 in the system of FIG. 2 in order to produce the wet particles/droplets 108 from the slurry. FIG. 4 is a cross-sectional view of a distal end of the two-fluid atomizer 200 of FIG. 3, and FIG. 5 is a perspective, exploded view of certain components of the distal end of the two-fluid atomizer 200 of FIG. 4.

The two-fluid atomizer 200 includes a body 202 having a proximal end 204 and a distal end 206. A channel 208 extends through the body 202 and includes an inlet 210, generally near the proximal end 204 of the body 202, and an outlet 212, generally near the distal end 206 of the body 202. The channel 208 operates to convey a first of the two-fluids, i.e., the slurry, from the inlet 210 to the outlet 212.

The two-fluid atomizer 200 also includes at least one electrode 214 operating to contact the slurry and apply an electrostatic charge thereto, such that the two-fluid atomizer 200 operates to produce a plurality of electrostatically charged wet particles/droplets 108. In one or more embodiments, the at least one electrode 214 may be disposed within the body 202 of the two-fluid atomizer 200 such that the slurry contacts the electrode 214 and becomes electrostatically charged while flowing from the inlet 210 to the outlet 212 of the channel 208. As illustrated in FIG. 3, the electrode 214 may be disposed within the channel 208, preferably in a coaxial arrangement, such that a significant portion of the surface area of the electrode 214 is available for contact with the slurry. The electrode 214 may be inserted into the channel 208 by way of a threaded bore of the body 202 and complementary threaded shaft of the electrode 214, which when engaged, positions the electrode within the channel 208. A connection terminal 216 may be electrically and mechanically coupled to the electrode 214 in order to provide a means for connecting with the high voltage supply 104 and receiving voltage potential at the surface of the electrode 214.

With reference to FIGS. 3 and 4, the two-fluid atomizer 200 may include a nozzle 220 in fluid communication with the outlet 212 of the channel 208. In particular, the outlet 212 of the channel 208 includes a tube 224 sized and shaped to engage, and be received within, a complementary bore 226 at an inlet end 228 of the nozzle 220. The engagement of the tube 224 and bore 226 permits fluid communication of the slurry (which has been electrostatically charged) from the channel 208 into an internal volume 230 intermediately disposed within the nozzle 220. A sealing ring 232 may be employed to ensure a fluid tight seal between the tube 224 and the bore 226, even under fluid pressure. The nozzle 220 preferably includes a transition section 234 of reducing diameter (a tapering surface) extending from the internal volume 230 to a nozzle orifice 236. The nozzle orifice 236 is preferably of a generally cylindrical shape, including an internal bore of a size sufficient to produce wet particles/droplets 108 of desired size and shape once they succumb to surface tension forces.

The two-fluid atomizer 200 may further include a nozzle cap 222, which generally surrounds the nozzle 220 and permits the nozzle orifice 236 to extend through a bore 266 at a distal end thereof. The nozzle cap 222 includes an engagement feature at a proximal end thereof, which engages the distal end of the body 202. In particular, the nozzle cap 222 includes a threaded shank 238, which threads into a complementary threaded bore 240 of the body 202. A sealing ring 242 may be employed to ensure a fluid tight seal as between an internal surface 244 of the nozzle cap 222 and an external surface 246 of the nozzle 220, thereby forming an internal volume 248 therebetween.

The two-fluid atomizer 200 includes another channel 250 extending through the body 202, which includes an inlet 252, generally near the proximal end 204 of the body 202, and an outlet 254, generally near the distal end 206 of the body 202. The channel 250 operates to convey a second of the two-fluids, i.e., the non-heated air, from the inlet 252 to the outlet 254. The outlet 254 is in fluid communication with the internal volume 248 (between the internal surface 244 of the nozzle cap 222 and the external surface 246 of the nozzle 220). Thus, the channel 250 operates to convey the non-heated air from the proximal end 204 to the distal end 206 of the two-fluid atomizer 200. The flow of the non-heated air through the two-fluid atomizer 200 may be about 5100 m³/hr at an input pressure of about 130 psi.

As best seen in FIGS. 4-5, the nozzle 220 includes a tapered surface 260 on an exterior thereof, which is downstream of the exterior surface 246 and downstream of the internal volume 248. The nozzle cap 222 includes a complementary internal surface in abutment with the tapered surface 260. A number of grooves (recesses) 262 are disposed in the tapered surface 260 and extend from the internal volume 248 toward the nozzle orifice 236. When the complementary internal surface of the nozzle cap 222 is in abutment with the tapered surface 260, the grooves 262 provide fluid communication of the non-heated air from the internal volume 248 toward the nozzle orifice 236. The grooves terminate at an annular space 264 between a peripheral edge of the tapered surface 260 and the outer surface of the nozzle orifice 236, where the nozzle orifice 236 exits the nozzle 220. The annular space 264 is in fluid communication with the bore 266, whereby a suitably sized bore (larger than a diameter of the nozzle orifice 236) permits the non-heated air to exit the nozzle 220 and nozzle cap 222 under pressure. Preferably, the grooves 262 extend such that they terminate tangentially to the annular space 264 and thereby cause the non-heated air to produce a swirling fluid motion within the space 264 and in the vicinity of the nozzle orifice 236 after it has exited the bore 266.

The swirling fluid motion of the non-heated air, as it leaves the nozzle 220 and nozzle cap 222, imparts a swirling agitation to the plurality of wet particles/droplets 108 as they leave the nozzle 220. Such swirling agitation may suspend and agitate the wet particles/droplets 108 in order to achieve the aforementioned fission and evaporation. The above approach to atomization enables relatively high slurry throughput, on the order of 1-20 kg/hr at an input pressure of about 20-100 psi.

Figure 6:
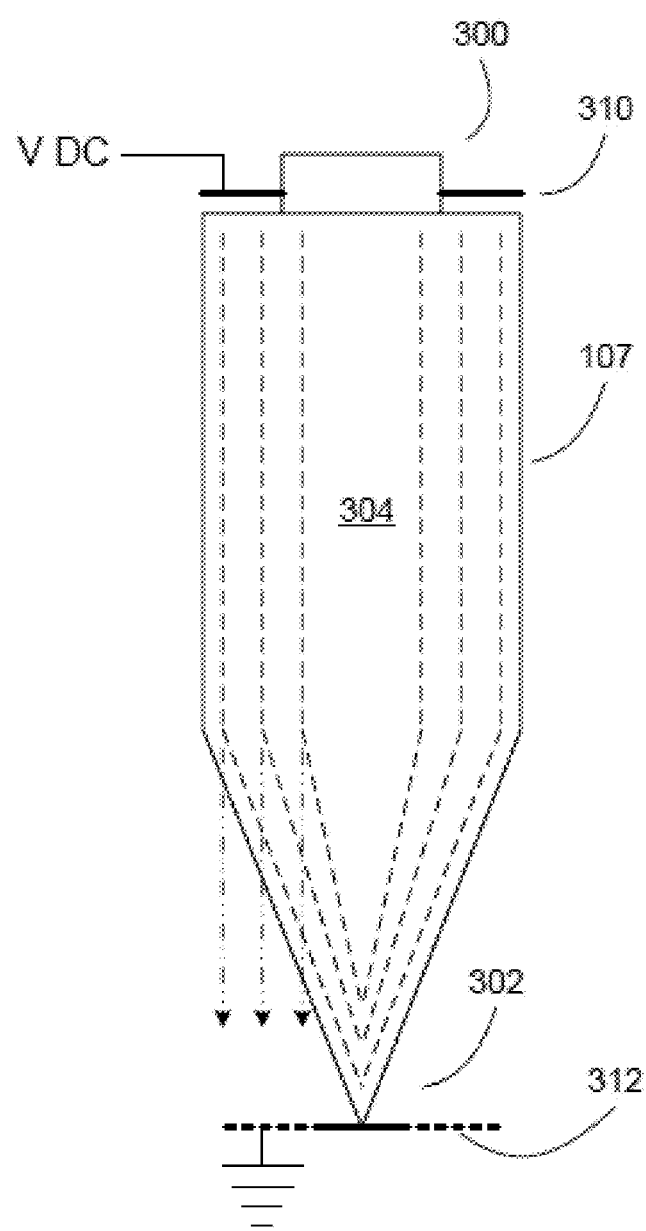
FIG. 6 is a schematic, side view of a drying chamber that may be employed in the system of FIG. 2 in accordance with one or more aspects of the present invention.
Figure 7:
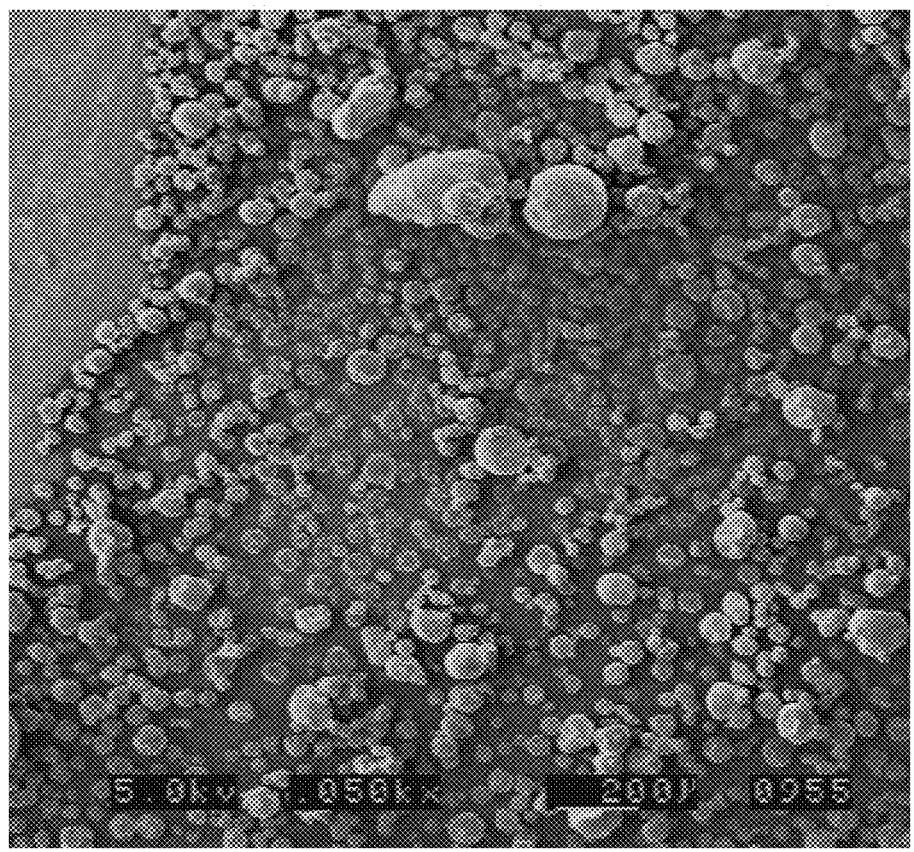
FIG. 7 is an image of dried powder non-fibrous particles produced using the system of FIG. 2.
Figure 8:
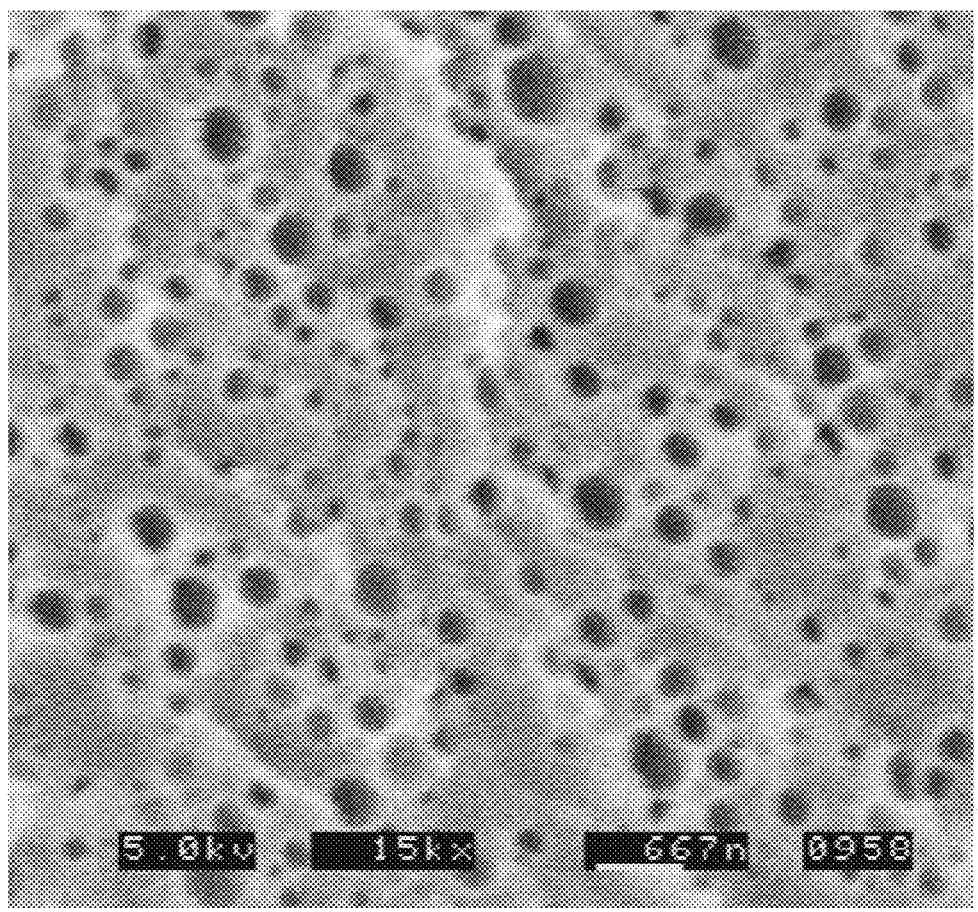
FIG. 8 is an image of a cross-section through one of the dried powder particles of FIG. 7 showing the encapsulation of the load within the carrier.
Figure 9:
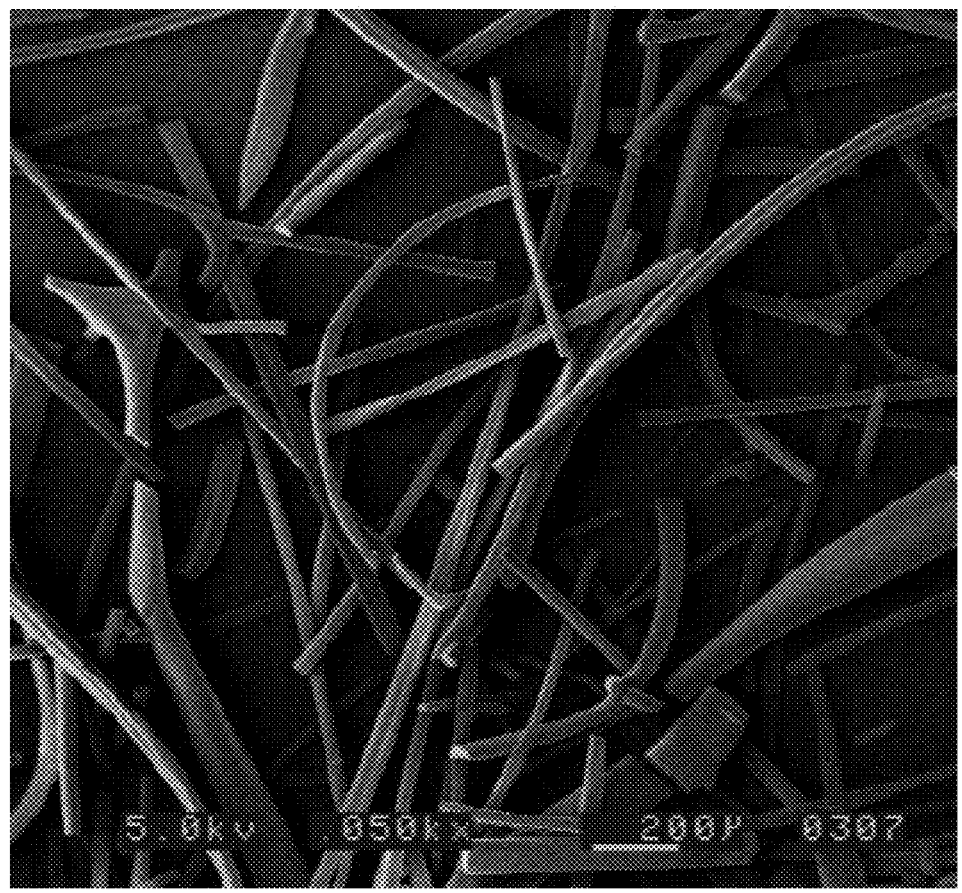
FIG. 9 is an image of dried powder fibers produced using the system of FIG. 2.
Figure 10:
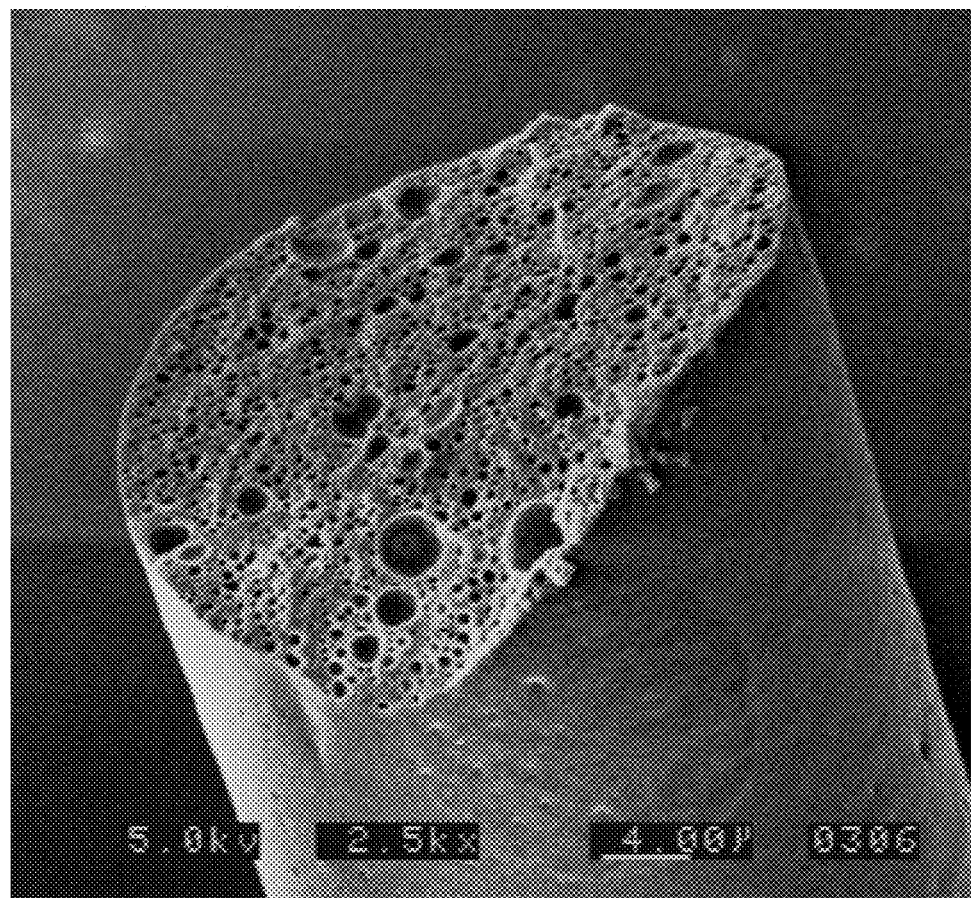
FIG. 10 is an image of a cross-section through one of the dried powder fibers of FIG. 9 showing the encapsulation of the load within the carrier.
Figure 11:
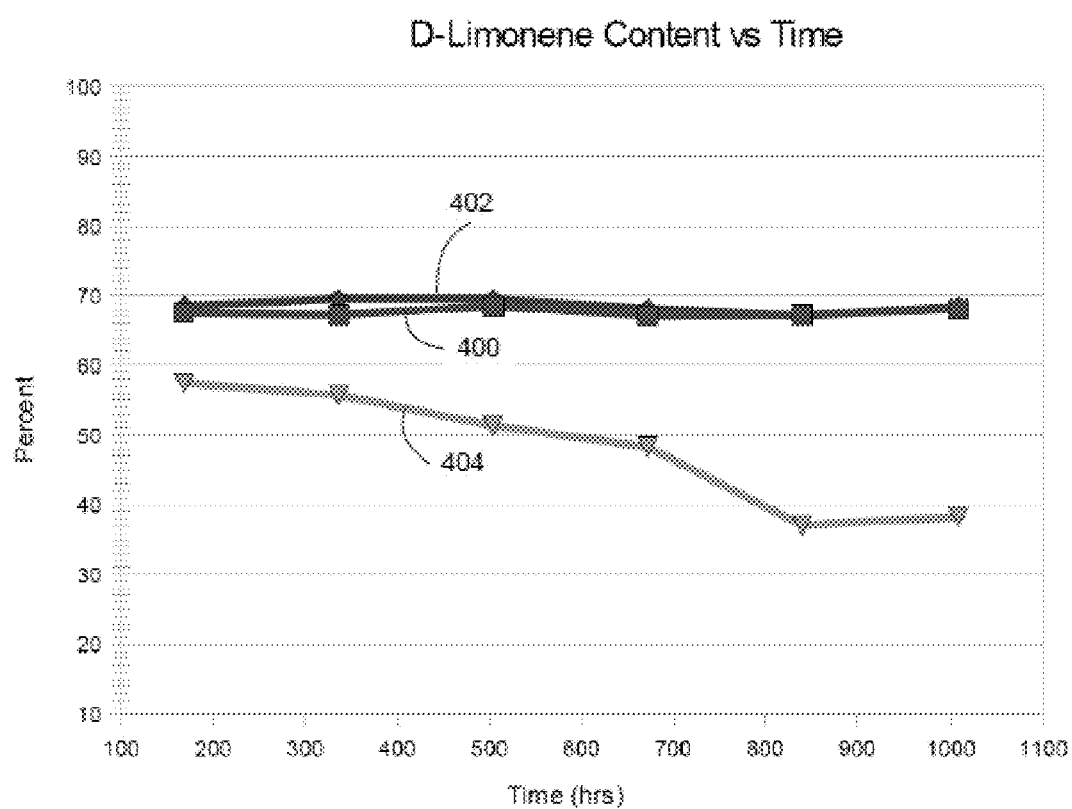
FIG. 11 is a graph illustrating certain properties of dried powder particles produced using the system of FIG. 2 as compared with the conventional spray drying process.

Reference is now made to FIG. 6, which is a schematic, side view of a drying chamber 107 that may be employed in the system 100 of FIG. 2 in accordance with one or more aspects of the present invention. The drying chamber 107 may include an inlet end 300, an outlet end 302, and an internal volume 304, within which the wet particles/droplets 108 are dried. The drying chamber is formed from a non-electrically conductive material. It is noted that the choice of materials (in this case a non-electrically conductive material, a non-metal) is not a mere matter of obvious design choice. Indeed, the conventional wisdom of the prior art spray drying process requires heated air (on the order of 200° C.), which consequently requires a metal drying chamber (typically stainless steel), otherwise the chamber would warp or otherwise fail.

A benefit of using non-heated air (which is directly counter to the conventional wisdom in the spray drying art) is that the drying chamber 107 may be formed from a non-metallic material; indeed, the temperature inside the drying chamber 107 may be less than 50° C. Thus, materials such as polymer-based composites may be employed for implementing the basic drying chamber 107. By way of example, filament wound fiberglass composite tanks (which are used for storage of water, various food stuffs, grain storage, brines and many non-food based applications) have excellent load carrying properties and can be used for making very large tanks. In one or more embodiments, such filament wound fiberglass composite materials may be used to fabricate the drying chamber 107 discussed herein. An advantage of using engineered plastics is the lower cost of the basic materials and the cost of manufacturing when compared to similar sized vessels made from stainless steel, for example. These materials also enable greater flexibility in the design of the drying chamber 107, making complex shapes possible, which are much more difficult and expensive to manufacture from stainless steel.

The use of non-metallic, non-conducting dielectric materials to form the drying chamber 107 (such as the engineered plastic composite materials), permits the use of one or more electric fields within the drying chamber 107 itself, to urge the particles/droplets 108 into desired trajectories and/or to urge such particles/droplets 108 from the inlet end 300 toward the outlet end 302 of the drying chamber 107. Notably, it is virtually impossible to develop an electric field inside a metallic, conductive vessel of the prior art because all charge accumulates on the surface of the vessel.

In accordance with one or more embodiments, the drying chamber 107 may include a first electrode 310 located at or near the inlet end 300 thereof, and a second electrode 312 located at or near the outlet end 302 of the drying chamber 107. The application of a source of voltage potential between the first and second electrodes 310, 312 induces an electric field (illustrated as broken lines) within the drying chamber 107 sufficient to urge the particles/droplets 108 into desired trajectories as they dry within the chamber 107. One such desirable trajectory is to cause the lines of the electric field to extend generally parallel to the walls of the drying chamber 107, even where such walls taper toward the outlet end 302. To achieve such trajectory, the second electrode 312 would have to be of a relatively small diameter as compared to the first electrode 310 (as is depicted by only the solid portion of the line of the electrode 312.) If the first and second electrodes 310, 312 are of generally the same diameter, then the lines of the electric field would extend generally parallel to the walls of the drying chamber 107, and then pass through the tapered walls at the outlet end 302. Other particle trajectories may be achieved based on number, location, size, and shape of the electrodes. As illustrated, the first and second electrodes 310, 312 may be disposed external to the drying chamber 107, yet induce an electric field within the internal volume 304 of the drying chamber 107 by virtue of the formation thereof from non-electrically conductive material.

To illustrate the utility of the no heat spray drying process for probiotic applications, Dannon™ Aunatural plain yogurt was subject to spray drying process described herein. In order to show that the bacteria (called *L. acidophilus*) survived the process, the spray dried yogurt was used to produce a new culture of yogurt. Since yogurt is approximately 85% water by weight, a slurry was formed using 643 grams of starch M180 and 357 grams of yogurt to make a 1 kg batch of slurry. The starch to yogurt ratio was about 1.8. The slurry was subject to the no-heat drying process discussed above with respect to FIG. 2 and related illustrations. The resulting powder was then mixed with milk and a new yogurt culture was produced. A control culture using some of the original yogurt was also made. The spray dried bacteria produced the same amount of culture as the control using comparable starting weights of bacteria.

Reference is now made to FIGS. 7-8, which respectively are an image of dried powder non-fibrous particles produced using the system of FIG. 2, and a cross-section through one of the dried powder particles of FIG. 7. As can be seen in the scanning electron images, the dried particle morphology benefits from a no-heat process in that the particles do not experience an abrupt rise in temperature as they enter the drying chamber and the particles do not exhibit cracks on the surface, volcano structures on the surface, or hollow regions within the particles. The cross-section of the particle shows a uniform distribution of encapsulated constituent component(s), in this case flavor oil droplets, in the micron-diameter range.

Reference is now made to FIGS. 9-10, which respectively are scanning electron images of dried powder fibers produced using the system of FIG. 2, and a cross-section through one of the dried powder fibers. Through modifications of the emulsion of the slurry, it is also possible to produce fibers instead of particles. For example, to make fibers one may change the carrier material (e.g., the starch) to a lower DE (dextrose equivalent), such that the concentration level at which an "entanglement transition" occurs is crossed. At such concentration level, the large starch molecules interact in a manner such that the slurry begins to manifest extensional viscoelastic properties that permit fibers to form. As can be seen in the scanning electron images, the dried fiber morphology is also characterized by a lack of cracks on the surface, volcano structures on the surface, or hollow regions within the fibers. The cross-section of the fiber also shows a uniform distribution of encapsulated constituent component(s), in this case flavor oil droplets, in the micron-diameter range.

Reference is now made to FIG. 11, which is a graph illustrating the weight percentage of the desired component(s) within dried powder particles produced using the system of FIG. 2 as compared with the conventional spray drying process. The no-heat process has demonstrated higher levels of preservation of starting active ingredients such as volatile flavor molecules. FIG. 11 shows the results of a 1000 hour accelerated aging study (at elevated temperatures of about 95° F.) comparing powders produced by conventional spray dry processing and the no-heat process. In the illustrated results, amounts of a particular constituent component, in this case a principle molecular type called D-Limonene (obtained from orange oil), were measured in an un-processed source of flavor oil 400, dried powder 402 produced in accordance with the no-heat process described herein, and dried powder 404 produced in accordance with the prior art heated air process. As FIG. 11 clearly shows, the no-heat powder 402 retains essentially the same flavor oil composition as the original oil source 400 used to produce the starting slurry, whereas the conventionally spray dried powder 404 departs significantly from the original starting oil 400. Similar results were found for all other principal constituents of other flavor oils. Additionally, the appearance of degradation products was greatly diminished in the no-heat samples, resulting in longer projected shelf-life of the powder.

The above data reveal that not only are some of the structures and processes of the system 100 of FIG. 2 inventive, but the dried powder (or fiber) itself is inventive. Indeed, the resultant dried powder (or fiber) includes a plurality of dried particles/fibers, which individually contain an amount of final active ingredient encapsulated within a carrier resulting from drying the slurry, which contained an initial active ingredient, a liquid solvent and the carrier. The initial active ingredient includes one or more constituent components, at least one of which is among one or more principle molecular types from which at least one of a desirable food, flavor, fragrance, medicament, bacteria, probiotic, pigment, etc. is obtained. The final active ingredient includes one or more of the constituent components corresponding with those of the initial active ingredient as modified by the drying of the slurry. A weight percentage of at least one of the one or more principle molecular types in the final active ingredient is essentially the same (e.g., within about 5%, 4%, 3%, or 1% of a) weight percentage of the corresponding principle molecular types in the initial active ingredient.

Another way to characterize the inventive characteristics of the dried powder/fibers is that a weight percentage of at least one of the one or more principle molecular types in the active ingredient does not vary significantly (not by more than about 5%, 4%, 3%, 2%, or 1%) during aging of the dried powder during any period of elevated temperature of about 95° F. up to about 1000 hours.

The present disclosure provides a new method of spray drying, using a low temperature, e.g., "no heat", spray drying process that produces powder products with superior flavor retention and stability. The spray drying method of the present disclosure does not employ purposely heated gas for removing water from the atomized fluid droplets, as has been the case in previously employed spray drying operations. The spray drying method of the present disclosure instead uses unheated air, e.g., dehumidified air, to carry out high throughput atomization processes, utilizing unique dryer designs and high solids content (low water content) slurries/emulsions with extremely high viscosities (for example, viscosities in a range of from 500 to 10000 mPa-s) to produce powders dried at low temperatures, such as temperatures on the order of from 5 to 50° C.

In specific embodiments, the air utilized in the spray drying operation may have a relative humidity of 10% or less, e.g., less than 8%, 7%, 6%, 5%, 4%, 3%, 2%, or 1%. The dewpoint of such air may be in a range of from −20° C. to 5° C., such as in a range of from −15° C. to 5° C., from −12° C. to 3° C., from −12° C. to 0° C., from −12° C. to −5° C., or any other suitable dewpoint range appropriate to the spray drying operation.

The use of high solids content emulsions (with solids concentrations of at least 40% by weight, based on total weight of the emulsion, and preferably at least 50% by weight on the same total weight basis) in the low temperature, e.g., no heat, spray drying process of the present disclosure provides a host of desirable attributes to the final powders produced by the process, such as: (1) high particle density, with density greater than that of water (i.e., >1 g/cc), so that the particles readily sink into aqueous solution and become rapidly dissolved or suspended, (2) greater resistance to oxidation imparted by the higher solids content, (3) substantial energy efficiency from the use of high solids content slurries/emulsions coupled with low temperatures, since about half as much water is evaporated as compared to traditional spray drying processes, and (4) superior retention of high value active ingredients such as flavors or fragrances, as another substantial economic advantage brought about by low temperature drying and high solids content slurries/emulsions.

By contrast, conventional high temperature drying processes lose a significant amount of the highly volatile flavor or fragrance active constituents to evaporation and oxidation, resulting in powders with less desirable flavor and aroma attributes. These powders resulting from high temperature conventional processes are typically of small average diameter, e.g., on the order of 60-100 micrometers, are not fully dense, and are difficult to dissolve in aqueous solutions. Powders produced by the low temperature spray drying process of the present disclosure, by contrast, have large average diameters, such as on the order of 125-250 micrometers, are fully dense, and readily go into solution.

The spray drying process of the present disclosure as a consequence of its low temperature, e.g., no heat, character, may be utilized for preparation of spray dried products that contain highly volatile components, e.g., volatile active ingredients whose boiling points are less than 100° C., and may for example be less than 90° C., 80° C., 70° C., 65° C., 60° C., 55° C., 50° C., 45° C., 40° C., 35° C., or even lower.

The spray drying process of the present disclosure may be employed to form spray dried powders and fibers in which one or more of the principle molecular types include aldehydes such as acetaldehydes, valeraldehyde, iso-valeraldehyde, etc, dimethyl and other alkyl sulfides, acetates such as ethyl acetates and other alkyl acetates, proprionates such as ethyl proprionate, alkyl butyrates such as methyl butyrate and ethyl butyrate, ketones, esters, etc.

Spray dried powders and fibers of the present disclosure, wherein volatile active ingredient(s) are highly retained, may be incorporated into any suitable products, such as for example beverages, sports beverages, nutritional beverages, gums, dairy products, soups, sauces, condiments, baked goods, personal-care products, oral care products, detergents, fresheners, etc.

Spray dried powders and fibers of the present disclosure thus can be produced in which the final active ingredient includes one or more of the constituent components corresponding to those of the initial active ingredient as modified by the spray drying process, wherein the spray dried powder or fiber composition has at least one of the characteristics of (i) a weight percentage of at least one of the one or more principle molecular types in the final active ingredient which is within about 15% of a weight percentage of the corresponding principle molecular types in the initial active ingredient, and which may for example be within about 12%, 10%, 8%, 7%, 6%, 5%, 4%, 3%, 2% or 1% of the weight percentage of the corresponding principle molecular types in the initial active ingredient, and (ii) a weight percentage of at least one of the one or more principle molecular types in the final active ingredient which does not vary by more than about 15% during aging of the dried powder or fiber during any period of elevated temperature of about 95° F. up to about 1000 hours, and which may for example not vary by more than about 12%, 10%, 8%, 7%, 6%, 5%, 4%, 3%, 2% or 1% during such aging.

The present disclosure thus embodies a novel approach for slurry or emulsion formulation for use in a low/no heat spray drying process, resulting in greatly improved powder properties and sensory characteristics of taste, aroma, etc.

In addition to having broad utility for processing of a wide variety of natural and artificial products, the spray drying process of the present disclosure is useful in the context of increasing utilization of natural products, including the proliferating use of essential oils extracted from natural sources. Essential oils are composed of wide ranges of lipophilic and highly volatile components covering a diverse spectrum of chemical classes. Essential oils, however, are susceptible to conversion and degradation reactions. Heat and light exposure and oxygen availability can significantly impact essential oil integrity. The low temperature spray drying process of the present disclosure substantially mitigates the degrading effects of heat and oxidation on the encapsulated flavor oil, as is illustrated in the following examples.

EXAMPLE 1

D-Limonene Assessment

In order to demonstrate some of the important advantages of the "no heat" spray dry process over traditional spray dry processing, flavor powders prepared by both methods were subjected to an accelerated aging test. The test powders were placed into an oven maintained at a temperature of 95° Fahrenheit. Once every seven days a sample of each powder was analyzed via gas chromatography mass spectrometry (GC-MS) analysis to determine the presence or absence of key molecular constituents. The flavor oil for analysis was extracted from the powder samples using standard procedures.

The results for both conventionally spray dried and no heat spray dried powders were also compared to a control sample of the starting neat flavor oil ("Neat Oil") subjected to the same storage conditions as the powders. The test was run for a period of 9 weeks. This test simulates degradation processes that a powder will experience over its shelf life. The primary degradation processes are oxidation of key flavor molecules, with the oxidation products being the cause of spoilage and development of "off" taste in the product. The GC-MS comparison also reveals deficits in key flavor constituents due to evaporation that occurred during the spray dry processing as compared to the starting flavor oil control sample.

In this study a lemon-lime flavor oil was selected because it is highly representative of the key volatile essential oil flavor molecules (top notes) that are present in a wide range of citrus based flavors. These key flavor molecules are highly susceptible to oxidation, have low boiling points, and are easily evaporated.

The emulsions for both samples contained a 10% by weight load of the lemon-lime flavor oil. Both emulsions used a carrier starch and emulsifier. The spray drying emulsion in accordance with the present disclosure (Sample A, "Zoom") contained 30% water, 6% starch emulsifier, and the remainder was 54% starch (all percentages by weight, based on total weight of the composition) and was spray dried at an inlet air temperature of 42° C. The sample for traditional spray dry processing (Sample B, "Spray") was produced by Adron, Inc., (94 Fanny Rd, Boonton, N.J. 07005, USA), using the same lot of lemon lime flavor oil.

The most abundant and readily perceived molecule in citrus flavors is d-limonene. D-limonene is a volatile top note component, which adds to the fresh, light, lemon, orange, and sweet citrus notes in the flavor. A decrease of d-limonene concentration in the citrus flavor composition dramatically alters the citrus flavor in an undesirable manner. When citrus oils spoil it is primarily due to oxidation of d-limonene. Oxidation decreases the d-limonene concentration, thereby giving rise to various unwanted oxidation products, such as p-cymene, p-cymene-8ol, epoxides, menthadienols, and gamma-terpinene.

Figure 12:
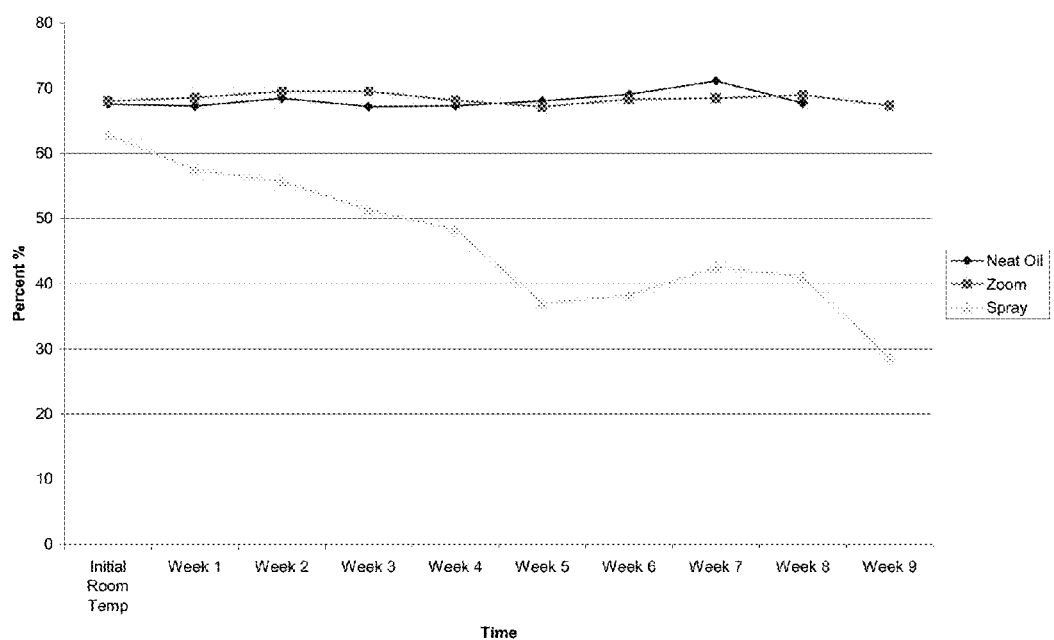
FIGS. 12-19 are graphs illustrating retention of properties by spray dried powders of the present disclosure.

FIG. 12 compares the mass spectrometric results for d-limonene content in the control neat lemon-lime oil ("Neat Oil"), the traditional spray dried powder (Sample B, "Spray") and the low temperature spray dried powder in accordance with present disclosure (Sample A, "Zoom"). In FIG. 12, d-limonene content is plotted as a function of time of exposure to hot air at a temperature of 95° F., over a period of 9 weeks. The traditional spray dry powder ("Spray") exhibited severe degradation of d-limonene, as compared to the control neat oil ("Neat Oil") and the low temperature dried powder of the present disclosure ("Zoom").

These results illustrate two important findings. First, the concentration of d-limonene in the traditional spray dried powder was lower than the control and the Zoom dried samples from the outset, reflecting the occurrence of evaporation that takes place during the traditional spray drying process due to the presence of heat as the powder is made. Second, as time progressed, the concentration of d-limonene continued to decrease in the traditionally spray dried sample, while the control neat oil and Zoom dried samples did not show any significant degradation.

EXAMPLE 2

Gamma-Terpinene Assessment

Figures 13, 14:
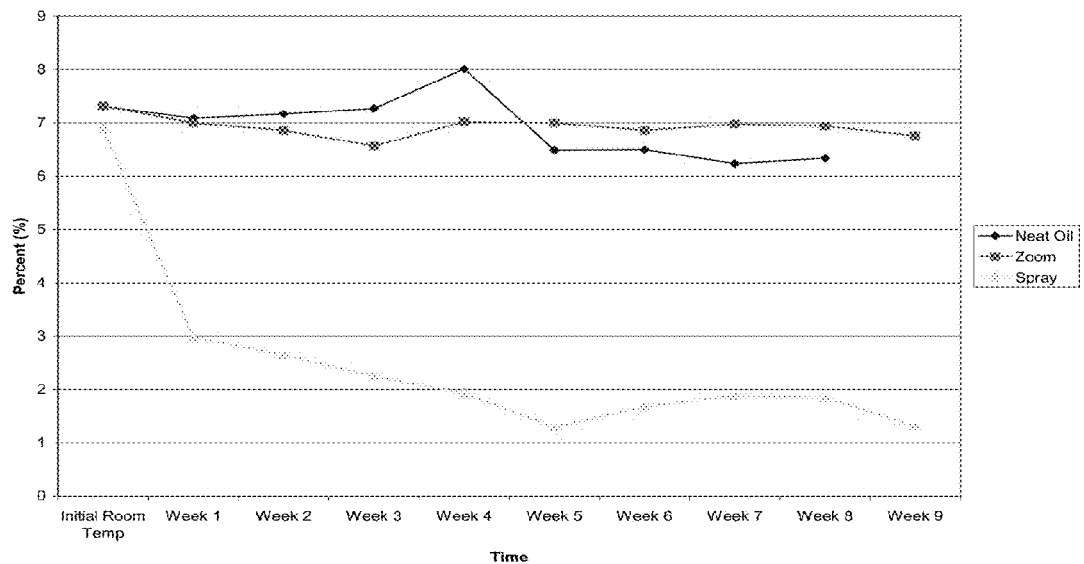

Gamma-terpinene is normally present in lemon and lime oils, and contributes to the top note of the flavor. When gamma-terpinene oxidizes the principal oxidation product is para-cymene (p-cymene). The concentration of gamma-terpinene as a function of time is shown in FIG. 13, for the control neat oil ("Neat Oil"), the traditional spray dried powder (Sample B, "Spray") and the low temperature spray dried powder in accordance with present disclosure (Sample A, "Zoom"). FIG. 13 shows a comparison of the gamma-terpinene content as a function of time of exposure to hot air at a temperature of 95° F. There was a relatively fast decrease in gamma-terpinene concentration in the traditional spray dried powder within the first two weeks of testing. The control neat oil and Zoom dried powder showed a slight decrease over the 9 week period.

FIG. 14 is a comparison of para-cymene oxidation product for corresponding samples of the he control neat oil ("Neat Oil"), the traditional spray dried powder (Sample B, "Spray") and the low temperature spray dried powder in accordance with present disclosure (Sample A, "Zoom"). The increased presence of p-cymene as seen in FIG. 14 is an indication of ongoing oxidation reactions. The presence of p-cymene produces an off-bitter tasting profile. As FIGS. 13 and 14 indicate, in the traditional spray dry powder, the gamma-terpinene concentration decreased just as quickly as the p-cymene concentration was increasing, reflecting a faster rate of oxidation in comparison to the Zoom dried powder and the control neat oil.

EXAMPLE 3

Alpha/Gamma Terpineol Assessment

Terpineols are a small constituent of citrus oils, which contribute to heavier, less fresh tastes. It is well known that alpha and gamma terpineols can be produced from limonene. The increased presence of alpha and gamma terpineol indicate ongoing oxidation processes.

Figure 15:
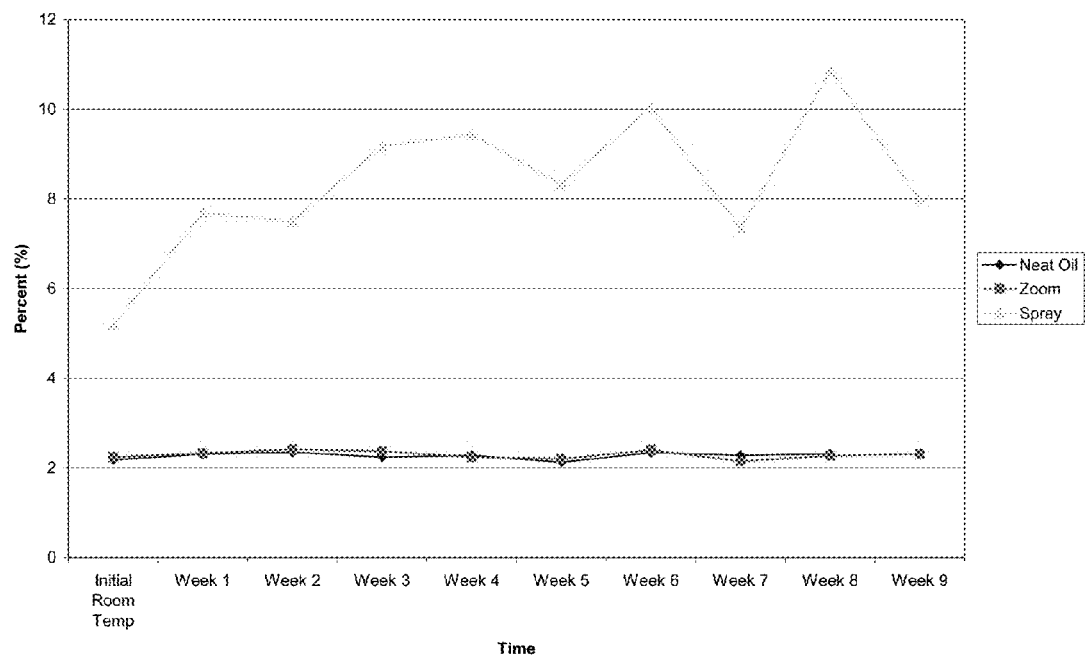

FIG. 15 shows the concentration of alpha and gamma terpineols as a function of time, for the control neat oil ("Neat Oil"), the traditional spray dried powder (Sample B, "Spray") and the low temperature spray dried powder in accordance with present disclosure (Sample A, "Zoom"). FIG. 15 shows a comparison of the alpha and gamma terpineols content as a function of time of exposure to hot air at a temperature of 95° F. There was a large initial rise in the concentration of terpineols in the powder made by the traditional spray dry process. The concentration of terpineols in the Zoom dried powder and in the control neat oil sample remained constant over the course of the test indicating very low or nonexistent terpineol production.

EXAMPLE 4

Limonene/Terpinolene Epoxide Formation and P-Menthadienol Formation

The formation of limonene and terpinolene epoxides and p-menthadienol are the result of oxidation processes. These unwanted byproducts form far more rapidly in traditional spray dry powders than in the control neat oil or the Zoom dried powder, as shown by the results in FIG. 16.

Figure 16:
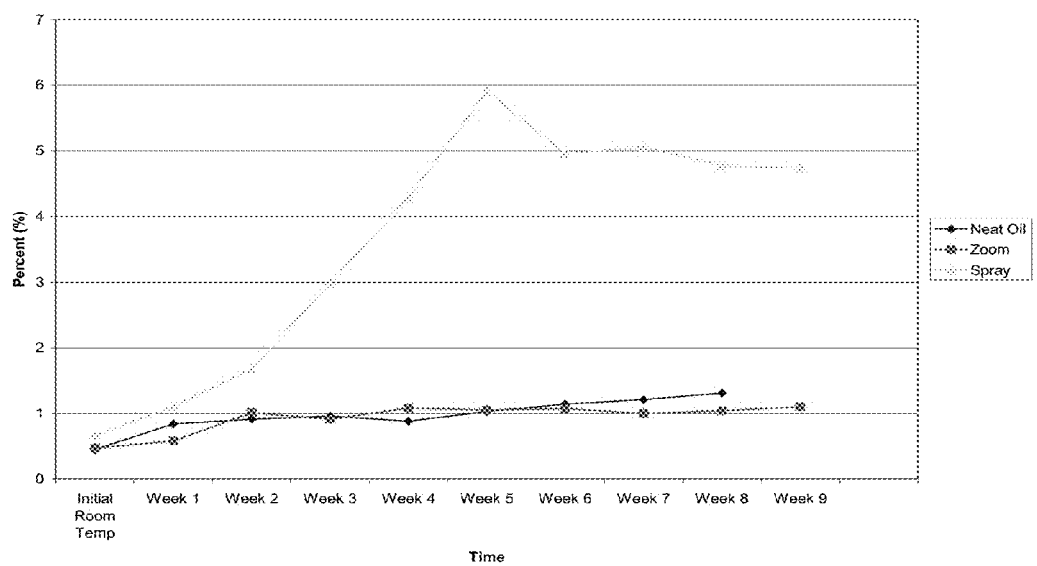

FIG. 16 shows the concentration of limonene and terpinolene epoxide as a function of time, for the control neat oil ("Neat Oil"), the traditional spray dried powder (Sample B, "Spray") and the low temperature spray dried powder in accordance with present disclosure (Sample A, "Zoom"). FIG. 16 shows a comparison of the limonene and terpinolene epoxide content as a function of time of exposure to hot air at a temperature of 95° F. The epoxide concentration increased rapidly over the first 5 weeks, indicating a more rapid rate of oxidation in the traditionally spray dried powder.

Figure 17:
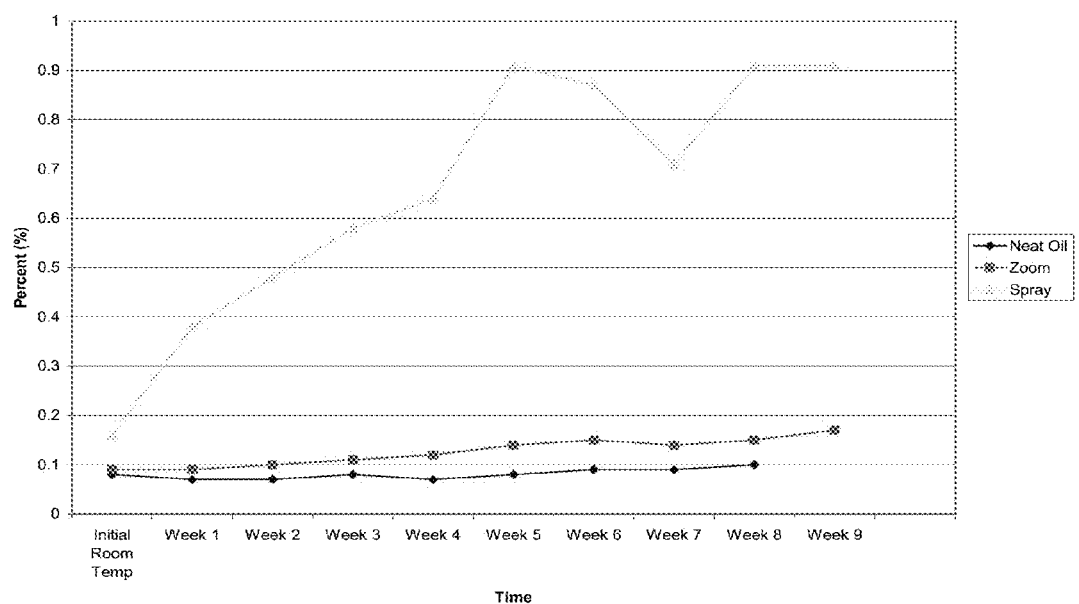

Similar results are shown in FIG. 17 in the concentration of p-menthadienol, for the control neat oil ("Neat Oil"), the traditional spray dried powder (Sample B, "Spray") and the low temperature spray dried powder in accordance with present disclosure (Sample A, "Zoom"), as a function of time of exposure to hot air at a temperature of 95° F. The data show a continuing rise in the concentration of p-menthadienol in the traditionally spray dried sample.

EXAMPLE 5

Trans- and Cis-Carveol Assessment

Trans- and cis-carveol are also formed as a result of oxidation of limonene. Their concentration in the neat oil is very low. When the concentration of these constituents becomes too high in a citrus oil, it indicates the occurrence of spoilage, and results in an off-taste.

Figure 18:
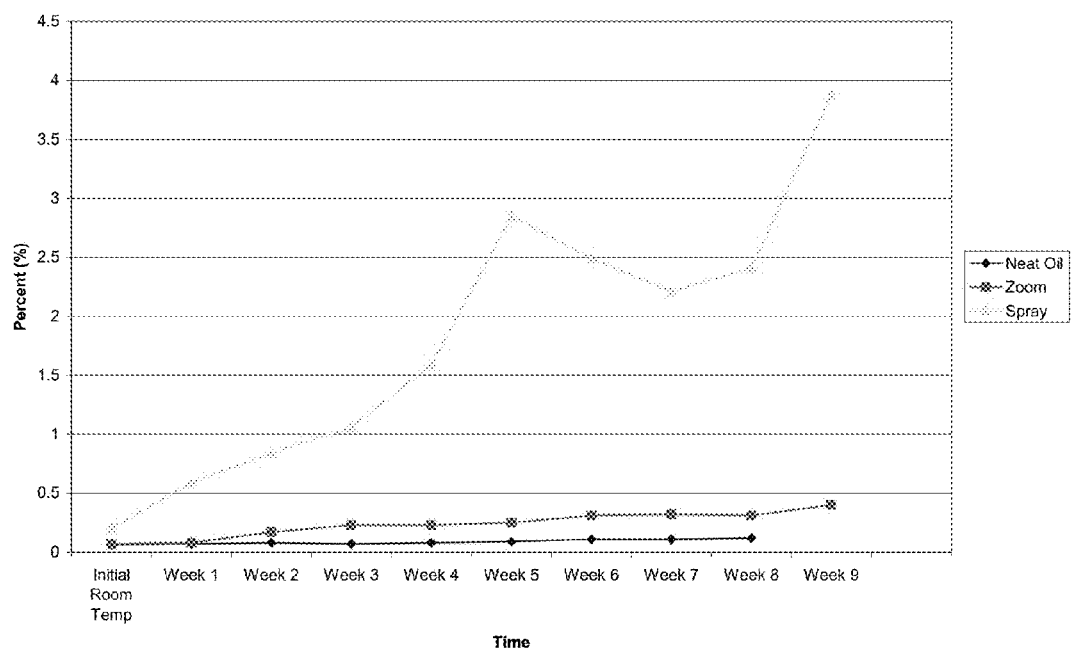

FIG. 18 shows the concentration of trans- and cis-carveol, for the control neat oil ("Neat Oil"), the traditional spray dried powder (Sample B, "Spray") and the low temperature spray dried powder in accordance with present disclosure (Sample A, "Zoom"), as a function of time of exposure to hot air at a temperature of 95° F. The data show that trans- and cis-carveol form at a much more rapid rate in the traditional spray dried powder than in either the control neat oil or in the Zoom dried powder.

EXAMPLE 6

P-Cymeme-8-Ol Assessment

This assessment involved the determination of the oxidation product p-cymene-8-ol in the control neat oil ("Neat Oil"), the traditional spray dried powder (Sample B, "Spray") and the low temperature spray dried powder in accordance with present disclosure (Sample A, "Zoom"), as a function of time of exposure to hot air at a temperature of 95° F.

Figure 19:
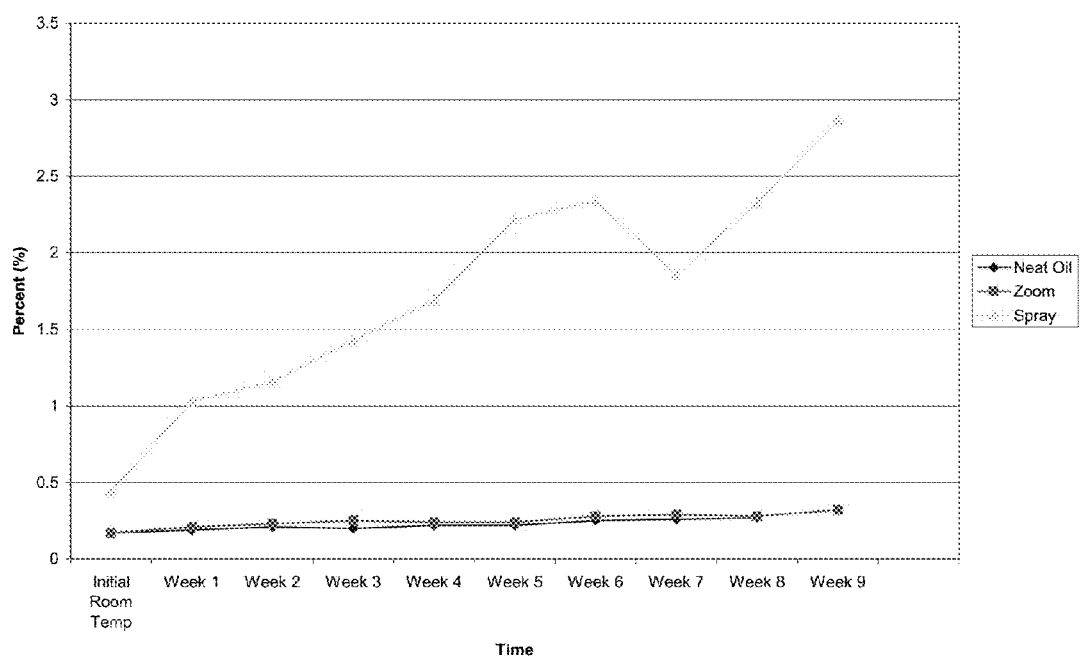

The results are shown in FIG. 19, as a graph of the concentration of p-cymene-8-ol, in weight percent, based on the weight of the sample, as a function of time for the 9 week assessment period. As shown by the data, the concentration of p-cymene-8-ol like p-cymene in the control neat oil was very low. Increases in concentration of p-cymene-8-ol are indicative of ongoing oxidation reaction. The increased formation of p-cymene-8-ol in the traditional spray dried powder when compared to the Zoom dried powder or the control neat oil, show that the spray dried sample was being oxidized faster than the Zoom dried sample, or the neat oil.

The foregoing empirical results show the substantially increased stability of spray dried products that is achievable by the "no heat" spray drying process of the present disclosure. These results show that such no heat spray drying process achieves extremely low loss of volatile flavor components that would otherwise occur as a result of evaporation and that the incidence of oxidative reactions in the spray dried powders of the present disclosure are greatly reduced, as compared with the levels that occur in traditional spray dried products. The spray dried powder products of the present disclosure retain dramatically higher levels of highly volatile and critical top note components of flavor oils. As a result, the shelf lives of spray dried powder products of the present disclosure greatly exceed those of traditional spray dried powder products.

What is claimed is:

1. A spray dried powder, comprising:
a plurality of dried particles, which individually contain an amount of final active ingredient encapsulated within a carrier resulting from drying a slurry containing an initial active ingredient, a liquid solvent and the carrier, wherein:
the initial active ingredient includes one or more constituent components, at least one of which is among one or more principle molecular types from which at least one of a desirable food, flavor, fragrance, medicament, and pigment is obtained;
the final active ingredient includes one or more of the constituent components corresponding with those of the initial active ingredient as modified by the drying of the slurry; and
a weight percentage of at least one of the one or more principle molecular types in the final active ingredient is within about 5% of a weight percentage of the corresponding principle molecular types in the initial active ingredient.

2. The spray dried powder of claim 1, wherein the one or more principle molecular types are molecular types of a food composition.

3. The spray dried powder of claim 1, wherein the one or more principle molecular types are molecular types of a flavor composition.

4. The spray dried powder of claim 1, wherein the one or more principle molecular types are molecular types of a fragrance composition.

5. The spray dried powder of claim 1, wherein the one or more principle molecular types are molecular types of a medicament composition.

6. The spray dried powder of claim 1, wherein the one or more principle molecular types are molecular types of a pigment composition.

7. The spray dried powder of claim 1, wherein the weight percentage of at least one of the one or more principle molecular types in the final active ingredient is within about 3% of a weight percentage of the corresponding principle molecular types in the initial active ingredient.

8. The spray dried powder of claim 1, wherein the weight percentage of at least one of the one or more principle molecular types in the final active ingredient is within about 2% of a weight percentage of the corresponding principle molecular types in the initial active ingredient.

9. The spray dried powder of claim 1, wherein the weight percentage of at least one of the one or more principle molecular types in the final active ingredient is within about 1% of a weight percentage of the corresponding principle molecular types in the initial active ingredient.

10. A spray dried powder, comprising:
a plurality of dried particles, which individually contain an amount of active ingredient encapsulated within a carrier, wherein:
the active ingredient includes one or more constituent components, at least one of which is among one or more principle molecular types from which at least one of a desirable food, flavor, fragrance, medicament, and pigment is obtained; and
a weight percentage of at least one of the one or more principle molecular types in the active ingredient does not vary by more than about 5% during aging of the dried powder during any period of elevated temperature of about 95° F. up to about 1000 hours.

11. The spray dried powder of claim 10, wherein the one or more principle molecular types are molecular types of a food composition.

12. The spray dried powder of claim 10, wherein the one or more principle molecular types are molecular types of a flavor composition.

13. The spray dried powder of claim 10, wherein the one or more principle molecular types are molecular types of a fragrance composition.

14. The spray dried powder of claim 10, wherein the one or more principle molecular types are molecular types of a medicament composition.

15. The spray dried powder of claim 10, wherein the one or more principle molecular types are molecular types of a pigment composition.

16. The spray dried powder of claim 10, wherein the weight percentage of at least one of the one or more principle molecular types in the active ingredient does not vary by more than about 3% during aging of the dried during any period of elevated temperature of about 95° F. up to about 1000 hours.

17. The spray dried powder of claim 10, wherein the weight percentage of at least one of the one or more principle molecular types in the active ingredient does not vary by more than about 2% during aging of the dried during any period of elevated temperature of about 95° F. up to about 1000 hours.

18. The spray dried powder of claim 10, wherein the weight percentage of at least one of the one or more principle molecular types in the active ingredient does not vary by more than about 1% during aging of the dried during any period of elevated temperature of about 95° F. up to about 1000 hours.

19. The spray dried powder of claim 10, wherein the carrier comprises starch.

20. A spray dried fiber composition, comprising:
a plurality of dried fibers, which individually contain an amount of final active ingredient encapsulated within a carrier resulting from drying a slurry containing an initial active ingredient, a liquid solvent and the carrier, wherein:
the initial active ingredient includes one or more constituent components, at least one of which is among one or more principle molecular types from which at least one of a desirable food, flavor, fragrance, medicament, and pigment is obtained; and
the final active ingredient includes one or more of the constituent components corresponding with those of the initial active ingredient as modified by the drying of the slurry, and wherein the spray dried fiber composition has at least one of the characteristics of (i) a weight percentage of at least one of the one or more principle molecular types in the final active ingredient is within about 5% of a weight percentage of the corresponding principle molecular types in the initial active ingredient, and (ii) a weight percentage of at least one of the one or more principle molecular types in the final active ingredient does not vary by more than about 5% during aging of the dried fibers during any period of elevated temperature of about 95° F. up to about 1000 hours.

* * * * *